US008263133B2

(12) United States Patent
Segura et al.

(10) Patent No.: US 8,263,133 B2
(45) Date of Patent: Sep. 11, 2012

(54) MULTIVALENT CLUSTERING TARGETING STRATEGY FOR DRUG CARRIERS

(75) Inventors: Tatiana Segura, Los Angeles, CA (US); Quinn Ng, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/708,520

(22) Filed: Feb. 18, 2010

(65) Prior Publication Data

US 2010/0266695 A1 Oct. 21, 2010

Related U.S. Application Data

(60) Provisional application No. 61/153,581, filed on Feb. 18, 2009.

(51) Int. Cl.
*A61K 9/14* (2006.01)
*A61K 38/00* (2006.01)
*A61K 48/00* (2006.01)
*C12N 15/11* (2006.01)

(52) U.S. Cl. ....... 424/489; 530/300; 977/773; 514/44 R; 514/44 A

(58) Field of Classification Search ........................ None
See application file for complete search history.

(56) References Cited

U.S. PATENT DOCUMENTS

| | | | |
|---|---|---|---|
| 2001/0001309 | A1 | 5/2001 | Scolastico et al. |
| 2002/0068695 | A1 | 6/2002 | Scolastico et al. |
| 2004/0136907 | A1 | 7/2004 | DeJong et al. |
| 2006/0241032 | A1 | 10/2006 | Bouwstra et al. |
| 2007/0293941 | A1 | 12/2007 | Gale et al. |
| 2008/0051835 | A1 | 2/2008 | Mazzocca et al. |
| 2008/0113910 | A1 | 5/2008 | Bouwstra et al. |
| 2008/0114078 | A1 | 5/2008 | Bouwstra et al. |
| 2008/0138278 | A1 | 6/2008 | Scherz et al. |
| 2008/0167446 | A1 | 7/2008 | Bouwstra et al. |
| 2008/0274957 | A1 | 11/2008 | Bouwstra et al. |
| 2008/0319114 | A1 | 12/2008 | Li et al. |
| 2009/0182063 | A1 | 7/2009 | Bouwstra et al. |
| 2009/0246133 | A1 | 10/2009 | Ruoslahti |
| 2010/0015058 | A1 | 1/2010 | Li et al. |
| 2010/0062531 | A1 | 3/2010 | De Boer et al. |
| 2010/0074844 | A1 | 3/2010 | Kolb et al. |
| 2010/0197585 | A1 | 8/2010 | Bevec et al. |
| 2010/0209382 | A1 | 8/2010 | Alexander-Bridges et al. |
| 2010/0222264 | A1 | 9/2010 | Bouwstra et al. |
| 2010/0234289 | A1 | 9/2010 | Majeti et al. |
| 2010/0272812 | A1 | 10/2010 | Arroyo et al. |

OTHER PUBLICATIONS

Arnold et al. (2004) "Activation of Integrin Function by Nanopatterned Adhesive Interfaces", *ChemPhysChem* 5:383-388.
Bettinger et al. (1999) "Size Reduction of Galactosylated PEI/DNA Complexes Improves Lectin-Mediated Gene Transfer into Hepatocytes", *Bioconjugate Chem.* 10: 558-561.
Blessing et al. (2001) "Different Strategies for Formation of PEGylated EGF-Conjugated PEI/DNA Complexes for Targeted Gene Delivery", *Bioconjugate Chem.*12: 529-537.
Carlson et al. (2007) "Selective Tumor Cell Targeting Using Low-Affinity, Multivalent Interactions", *ACS Chemical Biology* 2(2): 119-127.
Cavalcanti-Adam et al. (2006) "Lateral spacing of integrin ligands influences cell spreading and focal adhesion assembly", *European Journal of Cell Biology* 85: 219-224.
Chiu et al. (1999) "Structure of Adenovirus Complexed with Its Internalization Receptor, avb5 Integrin", *Journal of Virology* 73(8): 6759-6768.
Chiu et al. (2004) "Tumor-targeted gene delivery via anti-HER2 antibody (trastuzumab, HerceptinR) conjugated polyethylenimine", *Journal of Controlled Release* 97: 357-369.
Daniel et al. (2004) "Gold Nanoparticles: Assembly, Supramolecular Chemistry, Quantum-Size-Related Properties, and Applications toward Biology, Catalysis, and Nanotechnology", *Chem. Rev.* 104: 293-346.
Davis et al. (2002) "Non-viral gene delivery systems", *Current Opinion in Biotechnology* 13:128-131.
Diebold et al. (1999) "Mannose Polyethylenimine Conjugates for TargetedDNA Delivery into Dendritic Cells", *The Journal of Biological Chemistry* 274(27): 19087-19094.
Dijkgraaf et al. (2007) "Improved targeting of the $\alpha v\beta 3$ integrin by multimerisation of RGD peptides", *Eur J Nucl Med Mol Imaging* 34:267-273.
Erbacher et al. (1999) "Gene transfer with synthetic virus-like particles via the integrin-mediated endocytosis pathway", *Gene Therapy* 6: 138-145.
French et al. (2008) "Development of Human cloned Blastocysts Following Somatic Cell Nuclear Transfer (SCNT) with Adult Fibroblasts", *Stem Cells* 1-22; published online Jan. 17, 2008; doi:10.1634/stemcells.2007-0252.
Garanger et al. (2005) "New Multifunctional Molecular Conjugate Vector for Targeting, Imaging, and Therapy of Tumors", *Molecular Therapy* 12(6):1168-1175.
Goldman et al. (1995) "Expression of avb5 Integrin Is Necessary for Efficient Adenovirus-Mediated Gene Transfer in the Human Airway", *Journal of Virology* 69(10): 5951-5958.
Guo et al. (1999) "Receptor-Targeted Gene Delivery ViaFolate-Conjugated Polyethylenimine", *AAPS Pharmsci* 1(4):1-7.
Hughes et al. (1998) "Integrin affinity modulation", *Trends in Cell Biology* :359-364.
Humphries et al.(1996) "Integrin activation: the link between ligand binding and signal transduction", *Current Opinion in Cell Biology* 8:632-640.
Ingram et al. (1997) "Poly-hetero-ö-functionalized Alkanethiolate-Stabilized Gold Cluster Compounds", *J. Am. Chem. Soc.* 119(39):9175-9178.
Kichler et al. (2004) "Gene transfer with modified polyethylenimines", *J Gene Med* 6: S3-S10.
Kiessling et al. (2006) "Synthetic Multivalent Ligands as Probes of Signal Transduction", *Angew. Chem. Int. Ed.* 45, 2348-2368.

(Continued)

*Primary Examiner* — Janet Epps-Smith
(74) *Attorney, Agent, or Firm* — Tom Hunter; Weaver Austin Villeneuve & Sampson LLP

(57) ABSTRACT

The present invention provides clustered ligand vehicles for the delivery of a nucleic acid therapeutic agent to a target expressing a receptor. The invention further provides methods for treating a disease state by targeting a nucleic acid therapeutic agent to a target expressing a receptor using clustered ligand vehicles.

14 Claims, 29 Drawing Sheets

OTHER PUBLICATIONS

Kok et al. (2002) "Preparation and Functional Evaluation of RGD-Modified Proteins as avb3 Integrin Directed Therapeutics", *Bioconjugate Chem.* 2002, 13, 128-135.

Kong et al. (2007) "Nanoscale Cell Adhesion Ligand Presentation Regulates Nonviral Gene Delivery and Expression", *Nano Letters* 7(1): 161-166.

Koo et al. (2002) "Co-regulation of cell adhesion by nanoscale RGD organization and mechanical stimulus", *Journal of Cell Science* 115:1423-1433.

Kopatz et al. (2004) "A model for non-viral gene delivery: through syndecan adhesion molecules and powered by actin", *J Gene Med* 6: 769-776.

Kunath et al. (2003) "Integrin targeting using RGD-PEI conjugates for in vitro gene transfer", *J Gene Med* 5: 588-599.

Levy et al. (2004) "Rational and Combinatorial Design of Peptide Capping Ligands for Gold Nanoparticles", *J. Am. Chem. Soc.* 126: 10076-10084.

Luo et al. (2000) "Enhancement of transfection by physical concentration of DNA at the cell surface", *Nature Biotechnology* 18:893-95.

Maheshwari et al. (2000) "Cell adhesion and motility depend on nanoscale RGD clustering", *Journal of Cell Science* 113: 1677-1686.

Mathias et al. (1994) "Multiple Adenovirus Serotypes Use αv Integrins for Infection", *Journal of Virology* 68(10): 6811-6814.

McCarthy et al. (2008) "Multifunctional magnetic nanoparticles for targeted imaging and therapy", *Advanced Drug Delivery Reviews* 60: 1241-1251.

Medina-Kauwe (2003) "Endocytosis of adenovirus and adenovirus capsid proteins", *Advanced Drug Delivery Reviews* 55: 1485-1496.

Mislick et al. (1996) "Evidence for the role of proteoglycans in cation-mediated gene transfer", *Proc. Natl. Acad. Sci.* 93: 12349-12354.

Mizuguchi et al. (2002) "CAR- or αv integrin-binding ablated adenovirus vectors, but not fiber-modified vectors containing RGD peptide, do not change the systemic gene transfer properties in mice", *Gene Therapy* 9: 769-776.

Montet et al. (2006) "Multivalent Effects of RGD Peptides Obtained by Nanoparticle Display", *J. Med. Chem.* 49: 6087-6093.

Neu et al. (2005) "Recent advances in rational gene transfer vector design based on poly(ethylene imine) and its derivatives", *J Gene Med* 7: 992-1009.

Ogris et al. (1998) "The size of DNA/transferrin-PEI complexes is an important factor for gene expression in cultured cells", *Gene Therapy* 5: 1425-1433.

Ogris et al. (1999) "PEGylated DNA/transferrin-PEI complexes: reduced interaction with blood components, extended circulation in blood and potential for systemic gene delivery", *Gene Therapy* 6: 595-605.

Ogris et al. (2001) "DNA/polyethylenimine transfection particles: Influence of ligands, polymer size, and PEGylation on internalization and gene expression", *AAPS PharmSci* 3 (3): 1-11.

Rejman et al. (2008) "Gene Transfer by Means of Lipo- and Polyplexes: Role of Clathrin and Caveolae-Mediated Endocytosis", *Journal of Liposome Research* 16(3):237-247.

Schiffelers et al. (2003) "Anti-tumor efficacy of tumor vasculature-targeted liposomal doxorubicin", *Journal of Controlled Release* 91: 115-122.

Schiffelers et al. (2004) "Cancer siRNA therapy by tumor selective delivery with ligand-targeted sterically stabilized nanoparticle", *Nucleic Acids Research* 32(19): e149 1-10.

Srivastava et al. (2008) "Comparative evaluation of trimeric envelope glycoproteins derived from subtype C and B HIV-1 R5 isolates", *Virology* 372: 273-290.

Stewart et al. (1997) "Cryo-EM visualization of an exposed RGD epitope on adenovirus that escapes antibody neutralization", *The EMBO Journal* 16(6): 1189-1198.

Wang et al. (2005) "The Peptide Route to Multifunctional Gold Nanoparticles", *Bioconjugate Chem.* 16: 497-500.

Wickham et al. (1993) "Integrins αvβ3 and αvβ5 Promote Adenovirus Internalization but Not Virus Attachment", *Cell* 73: 309-319.

Zanta et al. (1997) "In Vitro Gene Delivery to Hepatocytes with Galactosylated Polyethylenimine", *Bioconjugate Chem.* 8: 839-844.

SEQUENCE LISTING

```
<160> NUMBER OF SEQ ID NOS: 6

<210> SEQ ID NO 1
<211> LENGTH: 6
<212> TYPE: PRT
<213> ORGANISM: Artificial Sequence
<220> FEATURE:
<223> OTHER INFORMATION: synthetic self-assembling peptide Cap

<400> SEQUENCE: 1

Cys Cys Val Val Val Thr
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic self-assembling peptide Cap-RGD

<400> SEQUENCE: 2

Cys Cys Val Val Val Thr Arg Gly Asp
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic self-assembling peptide Cap-RGD-ASA
<221> NAME/KEY: MOD_RES
<222> LOCATION: (9)...(9)
<223> OTHER INFORMATION: Asp modified by azidosalicylic acid (ASA)

<400> SEQUENCE: 3

Cys Cys Val Val Val Thr Arg Gly Asp
1               5

<210> SEQ ID NO 4
<211> LENGTH: 6
<212> TYPE: PRT
<213> ORGANISM: Artificial Sequence
<220> FEATURE:
<223> OTHER INFORMATION: synthetic self-assembling peptide Cap-ASA
```

-continued

```
<221> NAME/KEY: MOD_RES
<222> LOCATION: (6)...(6)
<223> OTHER INFORMATION: Thr modified by azidosalicylic acid (ASA)

<400> SEQUENCE: 4

Cys Cys Val Val Val Thr
 1               5

<210> SEQ ID NO 5
<211> LENGTH: 15
<212> TYPE: PRT
<213> ORGANISM: Artificial Sequence
<220> FEATURE:
<223> OTHER INFORMATION: synthetic peptide Cap-RGD
<221> NAME/KEY: MOD_RES
<222> LOCATION: (1)...(1)
<223> OTHER INFORMATION: N-acetylcysteine

<400> SEQUENCE: 5

Cys Cys Val Val Val Thr Gly Arg Gly Asp Ser Pro Ser Ser Lys
 1               5                  10                  15

<210> SEQ ID NO 6
<211> LENGTH: 13
<212> TYPE: PRT
<213> ORGANISM: Artificial Sequence
<220> FEATURE:
<223> OTHER INFORMATION: synthetic RGD peptide
<221> NAME/KEY: MOD_RES
<222> LOCATION: (1)...(1)
<223> OTHER INFORMATION: N-acetylglycine
<221> NAME/KEY: MOD_RES
<222> LOCATION: (13)...(13)
<223> OTHER INFORMATION: lysinamide

<400> SEQUENCE: 6

Gly Cys Gly Tyr Gly Arg Gly Asp Ser Pro Ser Ser Lys
 1               5                  10
```

MULTIVALENT CLUSTERING TARGETING STRATEGY FOR DRUG CARRIERS

CROSS-REFERENCES TO RELATED APPLICATIONS

This application claims priority to U.S. Provisional Application Ser. No. 61/153,581, filed on Feb. 18, 2009, which is incorporated herein by reference in its entirety.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

Arg-Gly-Asp (RGD) ligand clustering has been implicated in the modulation of cell adhesion, cell migration, cell spreading, and non-viral gene transfer [1-5]. For example, the maximum distance RGD ligands can be spaced for cell attachment and migration to occur on a flat surface is 58 nm [6] and it has been shown that integrin occupancy, conformation, and aggregation regulate integrin-signal transduction [7,8]. Interestingly, four different adenovirus sterotypes [9], have evolved to take advantage of clustered RGD ligands to gain access into cells through binding multiple integrin receptors simultaneously [10]. The clustered RGD ligands are displayed on five penton base proteins located at each of the twelve vertices of the virus surface. The penton base protein protrudes five RGD peptide sequences located 5.7 nm apart [9, 11], which have been found to be critical for viral cell entry [12]. Inhibition of the penton base protein using antibodies, RGD peptides, or by mutation results in decreased adenoviral internalization and overall transduction efficiency [11, 13-15].

The introduction of multivalent ligand binding to drug delivery carriers has been investigated as a method to enhance delivery of small molecular drugs [16] or tumor labeling agents [17] and has been demonstrated to have increased effects over monovalent binding [18-21]. However, the introduction of clustered ligand binding to non-viral gene delivery vectors has not been investigated. Nevertheless, ligands have been introduced to the surface of non-viral vectors to enhance targetability and overall gene transfer efficiency. These ligands include small molecules (e.g. folate and galactose), proteins (e.g transferrin and antibodies) [22] as well as RGD peptides [23, 24]. Although the direct RGD conjugation to DNA/poly(ethylene imine) (PEI) polyplexes increases the transfection efficiency in vitro and in vivo [23-25], the effect of RGD ligand clustering or the clustering of any other ligand on the efficiency and targetability of DNA/PEI polyplexes has not been investigated to date.

The cationic polymer PEI is one of the most widely used non-viral gene delivery vehicles for DNA, being used successfully both in vitro and in vivo [26]. It condenses with DNA through its positively charged amines, protecting DNA from degradation and forming particles (polyplexes) that can enter the cell and result in transgene expression [26]. The amines in PEI also serve as functional groups for chemical modification to introduce domains such as poly(ethylene glycol) to increase biocompatibility [27, 28], and ligands and peptides that enhance targeting, internalization and trafficking [29].

BRIEF SUMMARY OF THE INVENTION

In one aspect, the present invention provides a method for treating a disease state by targeting a nucleic acid therapeutic agent to a target expressing a receptor, the method comprising contacting the target with a composition comprising one or more nanoparticles, each nanoparticle being modified with a plurality of ligands, wherein the nucleic acid therapeutic agent is encapsulated in a carrier, and wherein each nanoparticle is conjugated to the surface of the carrier; thereby targeting the nucleic acid therapeutic agent to the target expressing the receptor. In one embodiment, the disease state being treated is cancer.

In one embodiment, each of the plurality of ligands comprises a small molecule, a protein, or a peptide. In one embodiment, each of the plurality of ligands comprises a peptide. In one embodiment, at least one of the plurality of ligands is capable of binding to the receptor.

In one embodiment, each of the plurality of ligands comprises self-assembling peptides. In one embodiment, the self-assembling peptides are selected from the group consisting of Cys-Cys-Val-Val-Val-Thr (Cap) (SEQ ID NO:1), Cys-Cys-Val-Val-Val-Thr-Arg -Gly-Asp (Cap-RGD) (SEQ ID NO:2), Cys-Cys-Val-Val-Val-Thr-Arg-Gly-Asp-Azidosalicylic Acid (Cap-RGD-ASA) (SEQ ID NO:3), and Cys-Cys-Val-Val-Val-Thr-Azidosalicylic Acid (Cap-ASA) (SEQ ID NO:4) peptides. In one embodiment, the self-assembling peptides comprise a mixture of Cap peptides and Cap-RGD peptides. In one embodiment, the Cap peptides and Cap-RGD peptides are present in a ratio of from about 99:1 to about 85:15. In one embodiment, the ratio of Cap peptides to Cap-RGD peptides can be selected for to promote clustering.

In one embodiment, each of the one or more nanoparticles is conjugated to the therapeutic agent by covalent bonding.

The peptides CCVVVT-COOH (Cap) (SEQ ID NO:1) and Ac-CCVVVTGRGDSPSSK-COOH (SEQ ID NO:5) (Cap-RGD peptide further comprising the SPSSK sequence (residues 11-15 of SEQ ID NO:5) which is referred to in the rest of this example as CAP-RGD) were purchased from Genscript Corporation at 98.5% and >95% purity respectively. Cap-RGD-ASA was synthesized by reaction of Cap-RGD peptide with N-Hydroxysuccinimidyl-4-azidosalicylic acid (NHS-ASA, Pierce, Rockford, Ill.). Cap-RGD peptide (1 µmol) was reacted with 1.5 mg of NHS-ASA in 10% DMSO/0.1 M carbonate buffer (pH 8.3) for 1 hour. The final solution was dialyzed in milliQ water and lyophilized. Cap-ASA was synthesized by acetylation of the N-terminus and reaction of Cap peptide with p-azidobenzoyl Hydrazide (ABH, Pierce, Rockford, Ill.). The photoreactive group on Cap-ASA is not exactly the same as the one present on Cap-RGD-ASA (varies by an extra OH group), but the chemistry they undergo is the same and, thus, they were given the same abbreviation. Cap peptide (1 µmol was dissolved in 6% DMSO in 0.1 M MES (pH 6.0) and 10 µL of 300 mM acetic anhydride in THF was added and vortexed for 3 min. Acetic anhydride addition was repeated twice. The solution was dialyzed in milliQ water and lyophilized. The lyophilized peptide was dissolved in 500 µL of 0.1 M MES (pH 6.0) and reacted with 0.2 mg EDC (Advanced ChemTech, Louisville, Ky.) and 0.3 mg NHS (Pierce, Rockford, Ill.) for 15 min. ABH was added to a final concentration of 5 mM and diluted to a final volume of 1 mL using PBS and reacted for 2 hrs. The solution was dialyzed in milliQ water and lyophilized.

In one embodiment, the nucleic acid therapeutic agent is selected from the group consisting of DNA, interfering RNA, small inhibitory RNA, and ribozymes. In one embodiment, the nucleic acid therapeutic agent is DNA. In one embodiment, the nucleic acid therapeutic agent is DNA and the carrier comprises poly(ethylene imine).

In one embodiment, the composition is not larger than 200 nm in diameter.

In one embodiment, each of the one or more nanoparticles is a gold nanoparticle.

In one embodiment, the target comprises blood, cells, tissues, or tumors. In one embodiment, the receptor is highly expressed by the target.

In another aspect, the present invention provides a clustered ligand vehicle for the delivery of a nucleic acid therapeutic agent to a target expressing a receptor, comprising: one or more nanoparticles, each nanoparticle being modified with a plurality of ligands; and the nucleic acid therapeutic agent encapsulated in a carrier, wherein each of the one or more nanoparticles is conjugated to the surface of the carrier.

In one embodiment, each of the plurality of ligands comprises a small molecule, a protein, or a peptide. In one embodiment, each of the plurality of ligands comprises a peptide. In one embodiment, at least one of the plurality of ligands is capable of binding to the receptor.

In one embodiment, each of the plurality of ligands comprises self-assembling peptides. In one embodiment, the self-assembling peptides are selected from the group consisting of Cys-Cys-Val-Val-Val-Thr (Cap) (SEQ ID NO:1), Cys-Cys-Val-Val-Val-Thr-Arg-Gly-Asp (Cap-RGD) (SEQ ID NO:2), Cys-Cys-Val-Val-Val-Thr-Arg-Gly-Asp-Azidosalicylic Acid (Cap-RGD-ASA) (SEQ ID NO:3), and Cys-Cys-Val-Val-Val-Thr-Azidosalicylic Acid (Cap-ASA) (SEQ ID NO:4) peptides. In one embodiment, the self-assembling peptides comprise a mixture of Cap peptides and Cap-RGD peptides. In one embodiment, the Cap peptides and Cap-RGD peptides are present in a ratio of from about 99:1 to about 85:15. In one embodiment, the ratio of Cap peptides to Cap-RGD peptides can be selected for to promote clustering.

In one embodiment, each of the one or more nanoparticles is conjugated to the therapeutic agent by covalent bonding.

In one embodiment, the carrier comprises a cationic polymer. In one embodiment, the carrier comprises poly(ethylene imine).

In one embodiment, the nucleic acid therapeutic agent is selected from the group consisting of DNA, interfering RNA, small inhibitory RNA, and ribozymes. In one embodiment, the nucleic acid therapeutic agent is DNA. In one embodiment, the nucleic acid therapeutic agent is DNA and the carrier comprises poly(ethylene imine).

In one embodiment, the clustered ligand vehicle is not larger than 200 nm in diameter.

In one embodiment, each of the one or more nanoparticles is a gold nanoparticle.

DETAILED DESCRIPTION OF THE INVENTION

I. Introduction

Figure 1A:
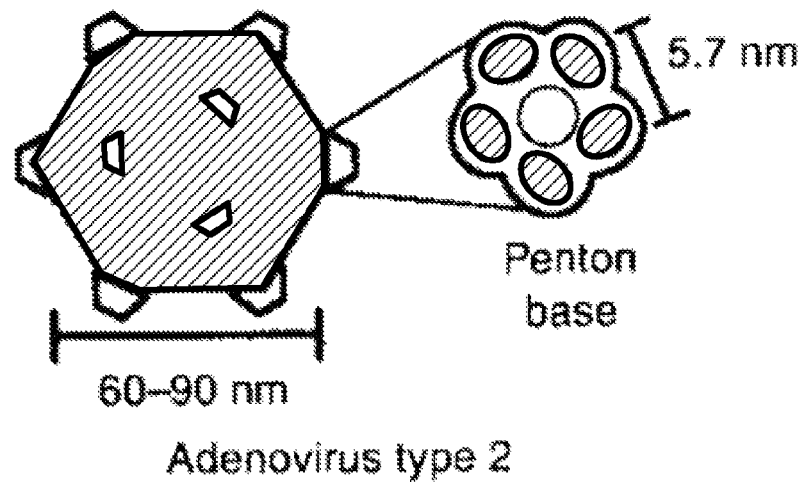
FIG. 1. Schematic comparing Adenovirus type 2 and DNA/PEI-Au-Cap-RGD-ASA polyplex. A. Type 2 Adenovirus with penton base proteins (reproduced from Stewart et al., EMBO J. 16:1189-98 (1997)). B. DNA/PEI-Au-Cap-RGD-ASA polyplex with RGD nanoclusters. C. Au-Cap-RGD-ASA nanoparticles are conjugated to preformed DNA/PEI polyplexes when exposed to UV light.

Non-viral vectors are often modified with ligands to enhance targeting and increase their overall gene transfer efficiency. Although PEI has been previously modified with ligands [23, 24, 31-37] to target corresponding receptors, the chemistries typically take advantage of the amine groups on the PEI backbone, resulting in ligands being unspecific and randomly distributed over the DNA/PEI polyplex. In contrast, here we explore an approach to modify PEI so that the ligands are clustered together and spatially constrained on the polyplex surface, allowing multiple ligands to bind to cell surface receptors simultaneously. For example, ligand modified gold nanoparticles can be attached to the surface of DNA/PEI polyplexes so they are presented as ligand clusters. Spatially constrained RGD peptides can be used to test our ligand clustering platform and examine the effect that clustered RGD ligands has on non-viral gene transfer to HeLa cells.

The present invention demonstrates for the first time that the presence of RGD nanoclusters on DNA/PEI polyplex surfaces enhances gene transfer and that the enhancement is dependent on the density of $\alpha_v\beta_3$ integrins on the cell surface, with higher $\alpha_v\beta_3$ densities resulting in higher luciferase transgene expression. This approach to introduce clustering is versatile and can be used to introduce alternative ligands to target other receptors by simply modifying the Cap peptide with the ligand of interest. Accordingly, the present invention provides clustered ligand vehicles for the targeted delivery of a nucleic acid therapeutic agent, comprising one or more nanoparticles modified with a plurality of ligands and conjugated to the surface of a carrier that encapsulates the nucleic acid therapeutic agent. The present invention also provides methods for targeting a nucleic acid therapeutic agent to a target expressing a receptor using clustered ligand vehicles.

II. Definitions

As used herein, the following terms have the meanings ascribed to them unless specified otherwise.

As used herein, the term "nanoparticle" refers to a defined particle of typically 5 to 5000, or more typically 5 to 500 atoms. Typical dimensions of the nanoparticles of the present invention are on the scale of a few nanometers, and can be tens of nanometers. The nanoparticles of the present invention typically have dimensions of less than 100 nanometers. In some embodiments, nanoparticles may be made from such materials as metal, such as silver or gold; semiconductor material; or carbon. In some embodiments, nanoparticles may be coated with materials such as natural polymers, synthetic polymers, surfactants, inorganic materials, and biological materials.

As used herein, the term "target" refers to a protein, substance, compound, or component in a biological sample. Targets include, but are not limited to, biomolecules and in particular proteins. The term "biomolecule" as used herein indicates a substance compound or component associated to a biological environment including, but not limited to, sugars, amino acids, peptides, proteins, oligonucleotides, polynucleotides, polypeptides, organic molecules, haptens, epitopes, biological cells, parts of biological cells, vitamins, hormones and the like.

As used herein, the term "nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

As used herein, the term "nucleic acid therapeutic agent" refers to nucleic acids that include a polynucleotide sequence that in whole or in part makes up a drug and can be used in human or animal therapeutic applications. Numerous nucleic acid therapeutic agents are known to practitioners of skill in the art including, without limitation, those disclosed herein.

As used herein, the terms "RNAi" and "siRNA" refer to a nucleic acid that forms a double stranded RNA, which double stranded RNA has the ability to reduce or inhibit expression of a gene or target gene when the siRNA expressed in the same cell as the gene or target gene. "siRNA" or "RNAi" thus refers to the double stranded RNA formed by the complementary strands. The complementary portions of the siRNA that hybridize to form the double stranded molecule typically have substantial or complete identity. In one embodiment, an siRNA refers to a nucleic acid that has substantial or complete identity to a target gene and forms a double stranded siRNA. Typically, the siRNA is at least about 15-50 nucleotides in length (e.g., each complementary sequence of the double stranded siRNA is 15-50 nucleotides in length), and preferably about 20-30 base nucleotides, preferably about 20-25 or about 24-29 nucleotides in length, e.g., 20, 21, 22, 23, 24, 25, 26, 27, 28, 29, or 30 nucleotides in length.

Figure 5A:
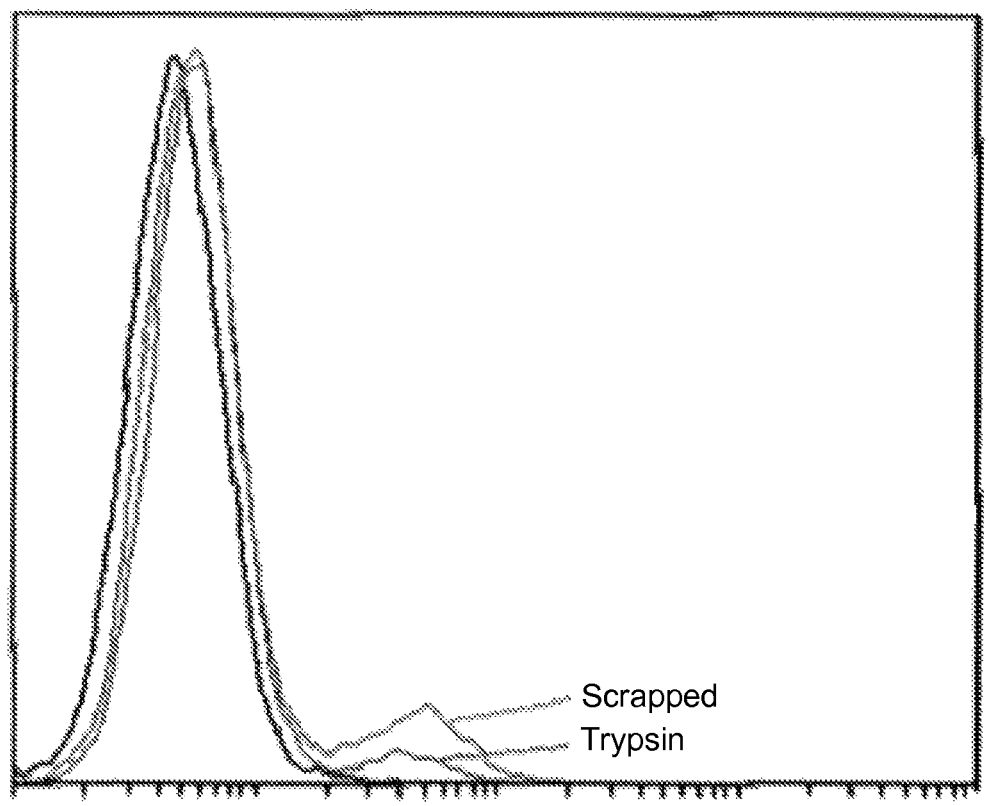
FIG. 5. Effects of multivalent nanoparticles on HeLa cells. A. Flow cytometry of $\alpha_v\beta_3$ integrin stained of HeLa cells passaged by scrapping or trypsinization measured 12 hrs after plating. A gate that included 5% of cells in the unstained control was used in determining the percent of cells that were $\alpha_v\beta_3$ integrin positive. The amount of trypsin and scrapped $\alpha_v\beta_3$ integrin positive cells are plotted with * representing p<0.0001 using a two-tailed t test (n=3). Mean fluorescence of all trypsin or scrapped cells were compared.  represents p<0.001 using a two-tailed t test (n=3). B. Anti adhesion assay of RGD peptide, Au-Cap, and Au-Cap-RGD nanoparticles with HeLa cells (n=3). The multivalent Au-Cap-RGD nanoparticles required less of the equivalent amount of RGD than monovalent free RGD peptide.
Figure 5A:
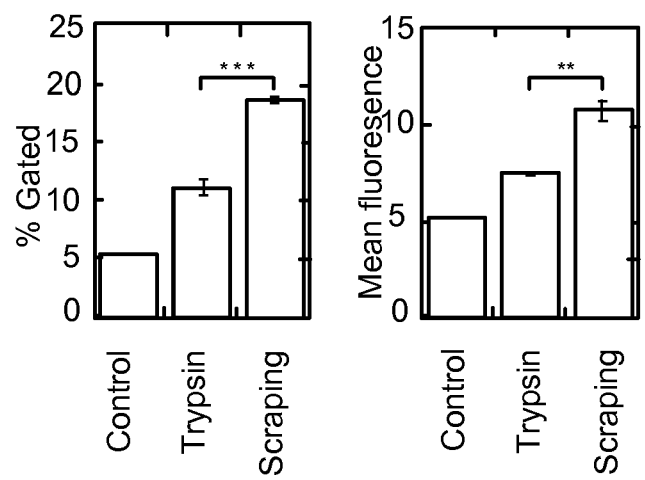

The design and making of siRNA molecules and vectors are well known to those of ordinary skill in the art. For instance, an efficient process for designing a suitable siRNA is to start at the AUG start codon of the mRNA transcript (e.g., see, FIG. 5) and scan for AA dinucleotide sequences (see, Elbashir et al. EMBO J. 20: 6877-6888 (2001). Each AA and the 3' adjacent nucleotides are potential siRNA target sites. The length of the adjacent site sequence will determine the length of the siRNA. For instance, 19 adjacent sites would give a 21 Nucleotide long siRNA siRNAs with 3' overhanging UU dinucleotides are often the most effective. This approach is also compatible with using RNA pol III to transcribe hairpin siRNAs. RNA pol III terminates transcription at 4-6 nucleotide poly(T) tracts to create RNA molecules having a short poly(U) tail. However, siRNAs with other 3' terminal dinucleotide overhangs can also effectively induce RNAi and the sequence may be empirically selected. For selectivity, target sequences with more than 16-17 contiguous base pairs of homology to other coding sequences can be avoided by conducting a BLAST search (see, www.ncbi.nlm.nih.gov/BLAST The siRNA can be administered directly or an siRNA expression vectors can be used to induce RNAi can have different design criteria. A vector can have inserted two inverted repeats separated by a short spacer sequence and ending with a string of T's which serve to terminate transcription. The expressed RNA transcript is predicted to fold into a short hairpin siRNA . The selection of siRNA target sequence, the length of the inverted repeats that encode the stem of a putative hairpin, the order of the inverted repeats, the length and composition of the spacer sequence that encodes the loop of the hairpin, and the presence or absence of 5'-overhangs, can vary. A preferred order of the siRNA expression cassette is sense strand, short spacer, and antisense strand. Hairpin siRNAs with these various stem lengths (e.g., 15 to 30) can be suitable. The length of the loops linking sense and antisense strands of the hairpin siRNA can have varying lengths (e.g., 3 to 9 nucleotides, or longer). The vectors may contain promoters and expression enhancers or other regulatory elements which are operably linked to the nucleotide sequence encoding the siRNA. The expression "control sequences" refers to DNA sequences necessary for the expression of an operably linked coding sequence in a particular host organism. The control sequences that are suitable for prokaryotes, for example, include but are not limited to a promoter, optionally an operator sequence, and a ribosome binding site. Eukaryotic cells are known to utilize promoters, polyadenylation signals, and enhancers. These control elements may be designed to allow the clinician to turn off or on the expression of the gene by adding or controlling external factors to which the regulatory elements are responsive.

Construction of suitable vectors containing the desired therapeutic gene coding and control sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and religated in the form desired.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the terms "peptide," "polypeptide" and "protein" are used interchangeably herein to refer to a polymer of amino acid residues. The terms apply to amino acid polymers in which one or more amino acid residue is an artificial chemical mimetic of a corresponding naturally-occurring amino acid, as well as to naturally-occurring amino acid polymers and non-naturally occurring amino acid polymers.

As used herein, the term "self-assembling peptide" refers to peptides that are able to spontaneously associate and form stable structures. In one embodiment, a self-assembling peptide of the present invention comprises an amino acid sequence of Cys-Cys-Val-Val-Val-Thr (SEQ ID NO:1) or conservatively modified variants thereof. In another embodiment, the self-assembling peptide of the present invention comprises an amino acid sequence of Cys-Cys-Val-Val-Val-Thr-Arg-Gly-Asp (SEQ ID NO:2) or conservatively modified variants thereof. Self-assembling peptides may further comprise other compounds, for example, compounds that mediate intermolecular bonding. In one embodiment, the self-assembling peptide of the present invention comprises the crosslinker azidosalicylic acid. In one embodiment, the self-assembling peptide is Cys-Cys-Val-Val-Val-Thr-Arg-Gly-Asp-Azidosalicylic Acid (SEQ ID NO:3). In one embodiment, the self-assembling peptide is Cys-Cys-Val-Val-Val-Thr-Azidosalicylic Acid (SEQ ID NO:4). One of skill in the art will recognize that other self-assembling peptides are useful in the present invention.

As used herein, the term "amino acid" refers to naturally occurring and synthetic amino acids, as well as amino acid analogs and amino acid mimetics that function in a manner similar to the naturally-occurring amino acids. Naturally-occurring amino acids are those encoded by the genetic code, as well as those amino acids that are later modified, e.g., hydroxyproline, ÿ-carboxyglutamate, and O-phosphoserine. Amino acid analogs refers to compounds that have the same basic chemical structure as a naturally occurring amino acid, i.e., an ÿ carbon that is bound to a hydrogen, a carboxyl group, an amino group, and an R group, e.g., homoserine, norleucine, methionine sulfoxide, and methionine methyl sulfonium. Such analogs have modified R groups (e.g., norleucine) or modified peptide backbones, but retain the same basic chemical structure as a naturally-occurring amino acid. Amino acid mimetics refers to chemical compounds that have a structure that is different from the general chemical structure of an amino acid, but that functions in a manner similar to a naturally-occurring amino acid.

Amino acids may be referred to herein by either their commonly known three-letter symbols or by the one-letter symbols recommended by the IUPAC-IUB Biochemical Nomenclature Commission. Nucleotides, likewise, may be referred to by their commonly accepted single-letter codes.

The term "conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

As used herein, the terms "identical" or percent "identity," in the context of two or more nucleic acids or polypeptide sequences, refer to two or more sequences or subsequences that are the same or have a specified percentage of amino acid residues or nucleotides that are the same (i.e., 70% identity, optionally 75%, 80%, 85%, 90%, 95%, 96%, 97%, 98%, or 99% identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 50 amino acids or nucleotides in length, or more preferably over a region that is 75-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

An example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A further indication that two polynucleotides are substantially identical is if the reference sequence, amplified by a pair of oligonucleotide primers or a pool of degenerate primers that encode a conserved amino acid sequence, can then be used as a probe under stringent hybridization conditions to isolate the test sequence from a cDNA or genomic library, or to identify the test sequence in, e.g., a northern or Southern blot. Alternatively, another indication that the sequences are substantially identical is if the same set of PCR primers can be used to amplify both sequences.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with a wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37 C, and a wash in 1×SSC at 45 C. A positive hybridization is at least twice background. Those of ordinary skill will readily recognize that alternative hybridization and wash conditions can be utilized to provide conditions of similar stringency.

As used herein, the terms "ligand" or "binding ligand" refer to a chemical or biological agent that is capable of binding to a target macromolecule, such as, cell-surface receptors of normal cells, cancer cells and endothelial cells, as well as acellular components in the extracellular matrix and the bony matrix, and surface receptors of infectious agents (virus, fungus, bacteria and parasite, among others). Binding ligands useful in the present invention include, but are not limited to, RGD peptide (binding to the $\alpha_5\beta_1$ and $\alpha_v\beta_3$ integrin receptors). One of skill in the art will appreciate that other binding ligands are useful in the present invention.

As used herein, the term "$\alpha_v\beta_3$ integrin" refers to a receptor of vitronectin. $\alpha_v\beta_3$ integrin serves as a receptor for a variety of extracellular matrix proteins displaying the arginine-glycine-aspartic acid (RGD) tripeptide sequence. These proteins include, for instance, vitronectin, fibronectin, fibrinogen, laminin, collagen, and Von Willibrand's factor.

The term "receptor" refers to a cell-associated protein that binds to a bioactive molecule termed a "ligand." This interaction mediates the effect of the ligand on the cell. Receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor). Membrane-bound receptors are characterized by a multi-domain structure comprising an extracellular ligand-binding domain and an intracellular effector domain that is typically involved in signal transduction. In certain membrane-bound receptors, the extracellular ligand-binding domain and the intracellular effector domain are located in separate polypeptides that comprise the complete functional receptor.

In general, the binding of ligand to receptor results in a conformational change in the receptor that causes an interaction between the effector domain and other molecule(s) in the cell, which in turn leads to an alteration in the metabolism of the cell. Metabolic events that are often linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids.

As used herein, the terms "overexpress," "overexpression" and "overexpressed," interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Overexpression can also be by 50%, 60%, 70%, 80%, 90% or more in comparison to a normal cell or comparison cell (e.g., tumorigenic cell).

As used herein, the term "contacting" is used interchangeably with the following: combined with, added to, mixed with, passed over, incubated with, flowed over, etc. Moreover, the clustered ligand vehicles of the present invention can be "administered" by any conventional method such as, for example, refer to parenteral, oral, topical, inhalation, intravenous, intraperitoneal, intramuscular, intralesional, intranasal or subcutaneous administration.

As used herein, the terms "sample" or "biological sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, Mouse; rabbit; or a bird; reptile; or fish.

As used herein, the term "subject" refers to animals such as mammals, including, but not limited to, primates (e.g., humans), cows, sheep, goats, horses, dogs, cats, rabbits, rats, mice and the like. In certain embodiments, the subject is a human.

As used herein, the terms "therapeutically effective amount or dose" or "therapeutically sufficient amount or dose" or "effective or sufficient amount or dose" refer to a dose that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins). In sensitized cells, the therapeutically effective dose can often be lower than the conventional therapeutically effective dose for non-sensitized cells.

As used herein, the term "cancer" refers to human cancers and carcinomas, sarcomas, adenocarcinomas, lymphomas, leukemias, etc., including solid tumors and lymphoid cancers, kidney, breast, lung, kidney, bladder, colon, ovarian, prostate, pancreas, stomach, brain, head and neck, skin, uterine, testicular, esophagus, and liver cancer, lymphoma, including non-Hodgkin's and Hodgkin's lymphoma, leukemia, and multiple myeloma.

III. Clustered Ligand Vehicles

The present invention provides clustered ligand vehicles for the targeted delivery of a nucleic acid therapeutic agent.

In some embodiments, the present invention provides clustered ligand vehicles for delivery of a nucleic acid therapeutic agent to a target expressing a receptor, comprising: one or more nanoparticles, each nanoparticle being modified with a plurality of ligands; and the nucleic acid therapeutic agent encapsulated in a carrier, wherein each of the one or more nanoparticles is conjugated to the surface of the carrier. The target can be any biological sample, and in some embodiments may be blood, cells, tissues, or tumors. In some embodiments, the biological sample is isolated from a subject.

In one aspect of the invention, the clustered ligand vehicle comprises one or more nanoparticles. In some embodiments, the nanoparticles are made from metal, for example gold or silver, or from semiconductor material. In some embodiments, the nanoparticles are gold nanoparticles. In some embodiments, the nanoparticles are coated with a material selected from the group consisting of natural polymers, synthetic polymers, surfactants, inorganic materials, and biological materials. In some embodiments, the nanoparticles are coated with an inorganic material. In some embodiments, the nanoparticles are coated with gold.

In another aspect of the invention, the nanoparticles are modified with a plurality of ligands. In some embodiments, each of the ligands comprises a small molecule, a protein, or a peptide. In some embodiments, each of the ligands comprises a peptide. In some embodiments, at least one of the ligands is capable of binding a receptor expressed by the target. In some embodiments, the ligand that is capable of binding to a receptor is a RGD ligand, which is capable of binding integrin receptors $\alpha_5\beta_1$ and $\alpha_v\beta_3$. In some embodiments, the peptides are self-assembling peptides. In some embodiments, the peptides are cap peptides comprising the amino acid sequence Cys-Cys-Val-Val-Val-Thr (SEQ ID NO:1). In some embodiments, the cap peptides further comprise azidosalicylic acid, and comprise the sequence Cys-Cys-Val-Val-Val-Thr-Azidosalicylic Acid (SEQ ID NO:4). In some embodiments the cap peptides further comprise a RGD ligand, and comprise the sequence Cys-Cys-Val-Val-Val-Thr-Arg-Gly-Asp (SEQ ID NO:2). In some embodiments the cap peptides further comprise a RGD ligand and azidosalicylic acid and comprise the sequence Cys-Cys-Val-Val-Val-Thr-Arg-Gly-Asp-Azidosalicylic Acid (SEQ ID NO:3).

The peptides described herein can be chemically synthesized using standard chemical synthesis techniques. In some embodiments the peptides are chemically synthesized by any of a number of fluid or solid phase peptide synthesis techniques known to those of skill in the art. Solid phase synthesis in which the C-terminal amino acid of the sequence is attached to an insoluble support followed by sequential addition of the remaining amino acids in the sequence is a preferred method for the chemical synthesis of the polypeptides of this invention. Techniques for solid phase synthesis are well known to those of skill in the art and are described, for example, by Barany and Merrifield (1963) *Solid-Phase Peptide Synthesis*; pp. 3-284 in *The Peptides: Analysis, Synthesis,*

Biology. Vol. 2: Special Methods in Peptide Synthesis, Part A.; Merrifield et al. (1963) *J. Am. Chem. Soc.*, 85: 2149-2156, and Stewart et al. (1984) *Solid Phase Peptide Synthesis*, 2nd ed. Pierce Chem. Co., Rockford, Ill.

The nanoparticle may be modified with different ratios of Cap peptides to Cap-RGD peptides. For example, the ratio of Cap to Cap-RGD may be from about 99:1 to about 85:15. The ratio of Cap to Cap-RGD may affect the density of RGDs on the surface of the nanoparticle, which may in turn affect the efficiency or specificity of the targeting of the clustered ligand vehicle. One of skill in the art will recognize that different Cap to Cap-RGD ratios may be desired depending on the particular application, and will be able to adjust the ratio of Cap to Cap-RGD to achieve the desired density of Cap-RGD peptides bound to the nanoparticle.

In another aspect of the invention, a nucleic acid therapeutic agent is encapsulated in a carrier. In some embodiments, the nucleic acid therapeutic agent is selected from the group consisting of DNA, interfering RNA, small inhibitory RNA, and ribozymes. In some embodiments the nucleic acid therapeutic agent is DNA. In some embodiments, antisense, siRNA, microRNA, or ribozyme sequences are delivered into the cell via a mammalian expression vector. For example, mammalian expression vectors suitable for siRNA expression are commercially available, for example, from Ambion (e.g., pSilencer vectors), Austin, Tex.; Promega (e.g., GeneClip, siSTRIKE, SiLentGene), Madison, Wis.; Invitrogen, Carlsbad, Calif.; InvivoGen, San Diego, Calif.; and Imgenex, San Diego, Calif. Typically, expression vectors for transcribing siRNA molecules will have a U6 promoter.

The nucleic acid therapeutic agent may be encapsulated by any of a number of vehicles, including but not restricted to liposomes, biodegradable polymers, hyrdogels, cyclodextrins (see, e.g., Gonzalez et al., 1999, Bioconjugate Chem., 10, 1068-1074; Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Patent Application Publication No. 2002/130430), biodegradable nanocapsules, and bioadhesive microspheres, or by proteinaceous vectors (O'Hare and Normand, International PCT Publication No. WO 00/53722). In some embodiments, the nucleic acid therapeutic agent of the invention can be encapsulated with polyalkylene imines. The alkyl can be, for example, methyl, ethyl, propyl, butyl, or any combination thereof. In some embodiments, the nucleic acid therapeutic agent of the invention can also be encapsulated or complexed with polyethyleneimine and derivatives thereof, such as polyethyleneimine-polyethyleneglycol-N-acetylgalactosamine (PEI-PEG-GAL) or polyethyleneimine-polyethyleneglycol-tri-N-acetylgalactosamine (PEI-PEG-triGAL) derivatives.

In yet another aspect of the invention, nanoparticles modified with a plurality of ligands are conjugated to the surface of the carrier. In some embodiments, the nanoparticles are conjugated to surface of the carrier by covalent bonding. In some embodiments, the crosslinker azidosalicylic acid is utilized to covalently conjugate the nanoparticles to the surface of the carrier upon exposure to ultraviolet light, as described herein.

IV. Methods for Targeting a Nucleic Acid Therapeutic Agent

The present invention also provides methods for treating a disease state by targeting a nucleic acid therapeutic agent to a target expressing a receptor. In some aspects the present invention provides methods for treating a disease state by administering a nucleic acid therapeutic agent to a target expressing a receptor. In some aspects the present invention provides methods of enhancing the efficiency of targeting and nucleic acid transfer by the nucleic acid therapeutic agent. In some aspects the present invention provides methods of enhancing the specificity of targeting and nucleic acid transfer by the nucleic acid therapeutic agent.

In one aspect of the invention, the target expresses a receptor. The receptor can be membrane-bound, cytosolic, or nuclear. In some embodiments the target expresses a high density of the receptor. In some embodiments the receptor to be targeted is a receptor that is highly expressed in tumors. In some embodiments the receptor expressed by the target is an integrin receptor. In some embodiments the receptor expressed by the target is the $\alpha_v\beta_3$ integrin. In some embodiments the $\alpha_v\beta_3$ integrin receptor is expressed at high levels. In some embodiments, the receptor is a protein whose expression is associated with a disease state, for example cancer. In some embodiments the receptor that is associated with a disease state is overexpressed. In some embodiments the receptor that is associated with a disease state is underexpressed.

In some embodiments, the invention provides a method of treating a disease state. In some embodiments, the disease state is cancer, particularly a cancer which expresses $\alpha_v\beta_3$ integrin, and the nucleic acid therapeutic agent which is administered to treat the cancer is targeted to $\alpha_v\beta_3$ integrin by RGD ligands that are clustered on nanoparticles and covalently bound to the carrier encapsulating the nucleic acid therapeutic agent. In some embodiments, the cancer is selected from the group consisting of breast cancer, gastric cancer, bladder cancer, ovarian cancer, thyroid cancer, lung cancer, prostate cancer, uterine cancer, testicular cancer, neuroblastoma, glioblastoma, squamous cell carcinoma of the head, neck, cervix and vagina, multiple myeloma, lymphoma, leukemia, and soft tissue and osteogenic sarcoma.

In another aspect of the invention, the nucleic acid therapeutic agent is administered to treat a disease state. The nucleic acid therapeutic agent is administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred. The administration may be local or systemic.

The compositions for administration will commonly comprise an agent as described herein (e.g., DNA, siRNA, ribozymes, and vectors thereof) dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs.

Thus, a typical pharmaceutical composition for intravenous administration will vary according to the agent. Actual methods for preparing parenterally administrable compositions will be known or apparent to those skilled in the art and are described in more detail in such publications as Remington's Pharmaceutical Science, 15th ed., Mack Publishing Company, Easton, Pa. (1980).

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that antibodies when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

Pharmaceutical formulations can be prepared by mixing the DNA, siRNA, ribozyme, or vector thereof having the desired degree of purity with optional pharmaceutically acceptable carriers, excipients or stabilizers. Such formulations can be lyophilized formulations or aqueous solutions. Acceptable carriers, excipients, or stabilizers are nontoxic to recipients at the dosages and concentrations used. Acceptable carriers, excipients or stabilizers can be acetate, phosphate, citrate, and other organic acids; antioxidants (e.g., ascorbic acid) preservatives low molecular weight polypeptides; proteins, such as serum albumin or gelatin, or hydrophilic polymers such as polyvinylpyllolidone; and amino acids, monosaccharides, disaccharides, and other carbohydrates including glucose, mannose, or dextrins; chelating agents; and ionic and non-ionic surfactants (e.g., polysorbate); salt-forming counter-ions such as sodium; metal complexes (e.g. Zn-protein complexes); and/or non-ionic surfactants.

The formulation may also provide additional active compounds, including, chemotherapeutic agents, cytotoxic agents, cytokines, growth inhibitory agent, and anti-hormonal agent. The active ingredients may also prepared as sustained-release preparations (e.g., semi-permeable matrices of solid hydrophobic polymers (e.g., polyesters, hydrogels (for example, poly (2-hydroxyethyl-methacrylate), or poly (vinylalcohol)), polylactides. The compounds may also be entrapped in microcapsules prepared, for example, by coacervation techniques or by interfacial polymerization, for example, hydroxymethylcellulose or gelatin microcapsules and poly-(methylmethacylate) microcapsules, respectively, in colloidal drug delivery systems (for example, liposomes, albumin microspheres, microemulsions, nano-particles and nanocapsules) or in macroemulsions.

The compositions can be administered for therapeutic or prophylactic treatments. In therapeutic applications, compositions are administered to a patient suffering from a disease (e.g., cancer) in a "therapeutically effective dose." Amounts effective for this use will depend upon the severity of the disease and the general state of the patient's health. Single or multiple administrations of the compositions may be administered depending on the dosage and frequency as required and tolerated by the patient. A "patient" or "subject" for the purposes of the present invention includes both humans and other animals, particularly mammals. Thus the methods are applicable to both human therapy and veterinary applications. In the preferred embodiment the patient is a mammal, preferably a primate, and in the most preferred embodiment the patient is human. Other known cancer therapies can be used in combination with the methods of the invention. For example, the compositions for use according to the invention may also be used to target or sensitize a cell to other cancer therapeutic agents such as 5FU, vinblastine, actinomycin D, cisplatin, methotrexate, and the like.

In other embodiments, the methods of the invention with other cancer therapies (e.g, radical prostatectomy), radiation therapy (external beam or brachytherapy), hormone therapy (e.g., orchiectomy, LHRH-analog therapy to suppress testosterone production, anti-androgen therapy), or chemotherapy. Radical prostatectomy involves removal of the entire prostate gland plus some surrounding tissue. This treatment is used commonly when the cancer is thought not to have spread beyond the tissue. Radiation therapy is commonly used to treat prostate cancer that is still confined to the prostate gland, or has spread to nearby tissue. If the disease is more advanced, radiation may be used to reduce the size of the tumor. Hormone therapy is often used for patients whose prostate cancer has spread beyond the prostate or has recurred. The objective of hormone therapy is to lower levels of the male hormones, androgens and thereby cause the prostate cancer to shrink or grow more slowly. Luteinizing hormone-releasing hormone (LHRH) agonists decrease the production of testosterone. These agents may be injected either monthly or longer. Two such analogs are leuprolide and goserelin. Anti-androgens (e.g., flutamide, bicalutamide, and nilutamide) may also be used. Total androgen blockade refers to the use of anti-androgens in combination with orchiectomy or LHRH analogs, the s combination is called. Chemotherapy is an option for patients whose prostate cancer has spread outside of the prostate gland and for whom hormone therapy has failed. It is not expected to destroy all of the cancer cells, but it may slow tumor growth and reduce pain. Some of the chemotherapy drugs used in treating prostate cancer that has returned or continued to grow and spread after treatment with hormonal therapy include doxorubicin (Adriamycin), estramustine, etoposide, mitoxantrone, vinblastine, and paclitaxel. Two or more drugs are often given together to reduce the likelihood of the cancer cells becoming resistant to chemotherapy. Small cell carcinoma is a rare type of prostate cancer that is more likely to respond to chemotherapy than to hormonal therapy.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

In therapeutic use for the treatment of cancer, the nucleic acid therapeutic agents utilized in the pharmaceutical method of the invention are administered at the initial dosage of about 0.001 mg/kg to about 1000 mg/kg daily. A daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The dosages, however, may be varied depending upon the requirements of the patient, the severity of the condition being treated, and the compound being employed. For example, dosages can be empirically determined considering the type and stage of cancer diagnosed in a particular patient. The dose administered to a patient, in the context of the present invention should be sufficient to effect a beneficial therapeutic response in the patient over time. The size of the dose also will be determined by the existence, nature, and extent of any adverse side-effects that accompany the administration of a particular vector, or transduced cell type in a particular patient. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. For convenience, the total daily dosage may be divided and administered in portions during the day, if desired.

The pharmaceutical preparations (e.g., DNAs, siRNAs, RNAis, and ribozymes) for use according to the invention are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine).

V. EXAMPLES

Example 1

Design and Characterization of Ligand Nanoclusters

RGD Nanocluster Formation and Characterization

Figure 1B:
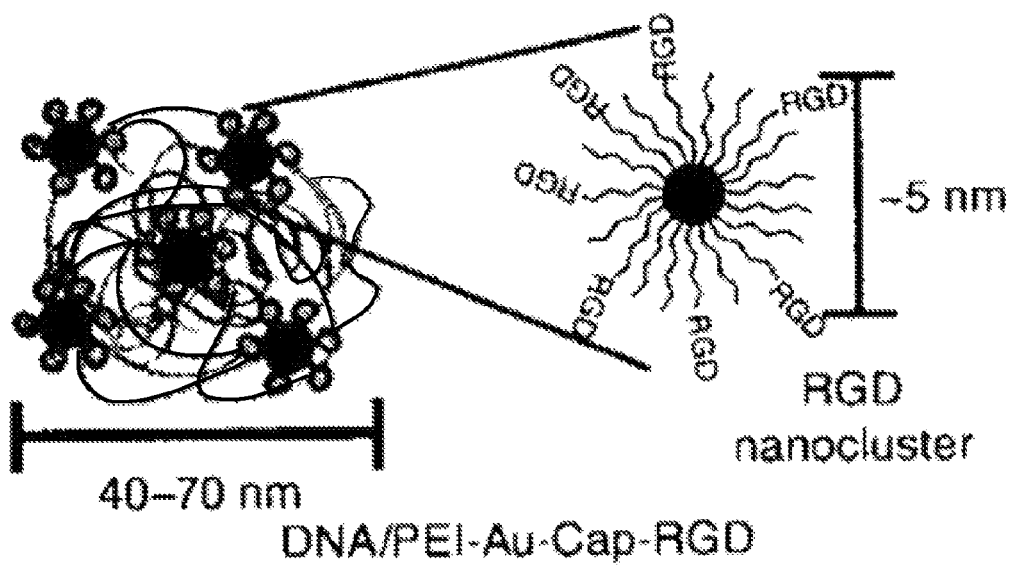
Figure 1C:
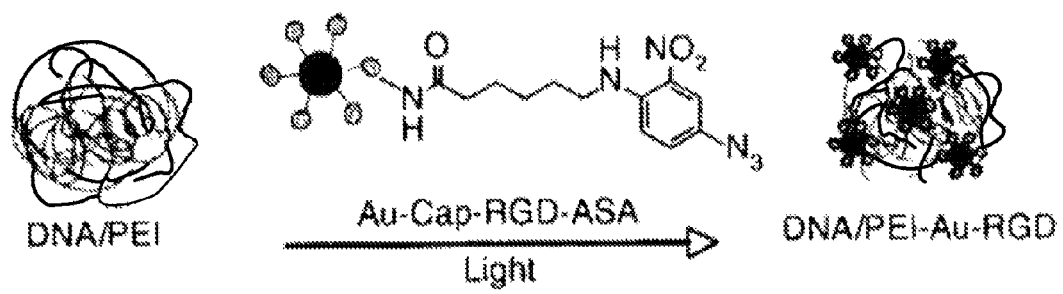
Figure 2A:
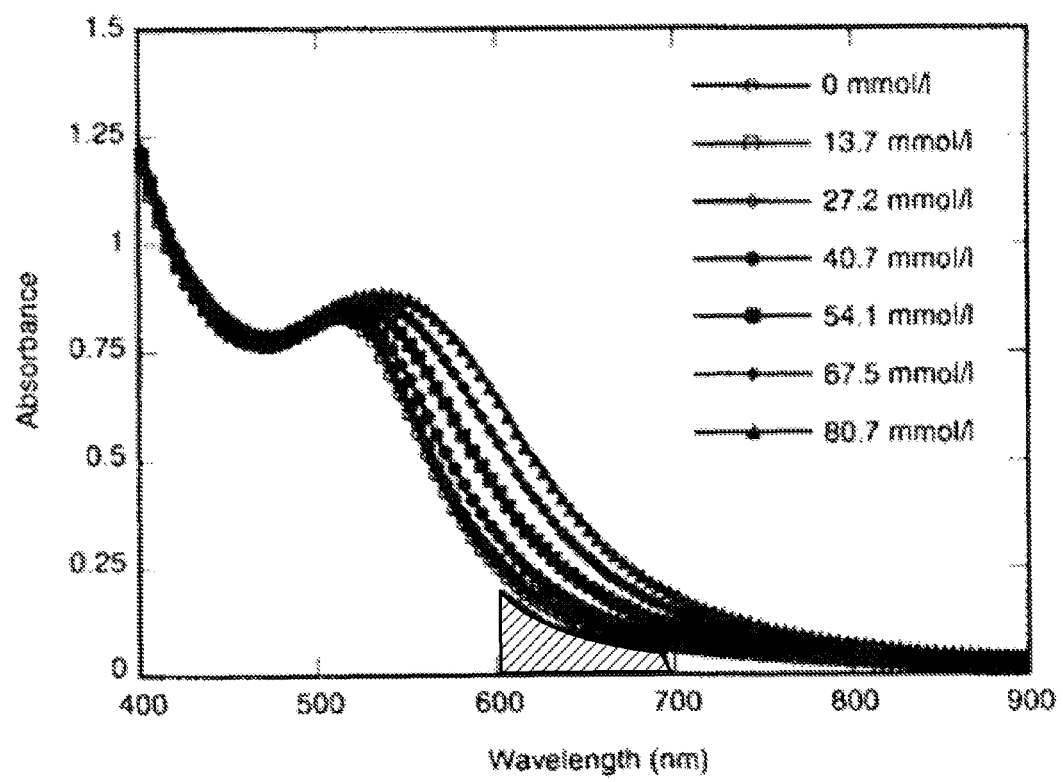
FIG. 2. Salt stability of modified and unmodified nanoparticles measured using UV-Vis absorbance spectroscopy. Salt concentration was increased using 2 μL for unmodified nanoparticles and 15 μL of 4.11 M NaCl every 15 min. Wavelength scans of (A) 5 nm unmodified Au nanoparticles and (B) Au-Cap nanoparticles in solution with increasing NaCl concentration. Shaded area under the curves in A and B were used to calculate aggregation parameter. C. Aggregation parameter plotted with mean±SD for n=3 for increasing NaCl concentration for 5 nm unmodified Au and Au-Cap. Aggregation parameter of unmodified Au show a large increase with small increases in NaCl concentration.
Figure 2B:
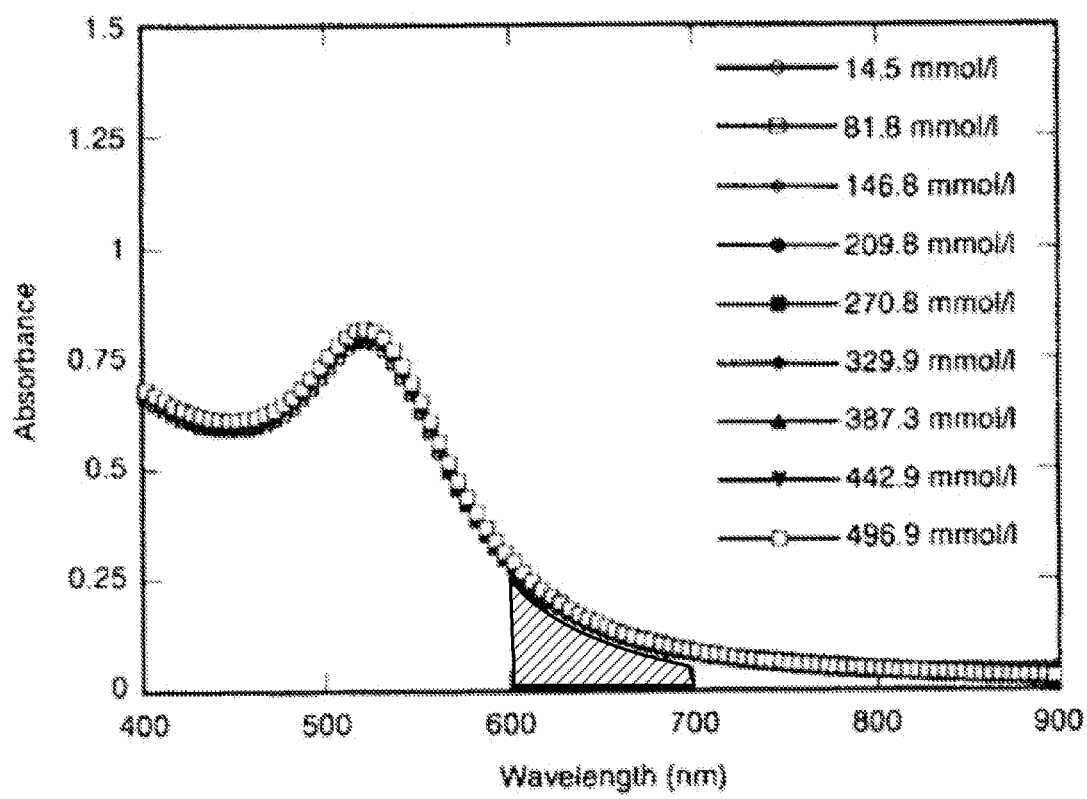
Figure 2C:
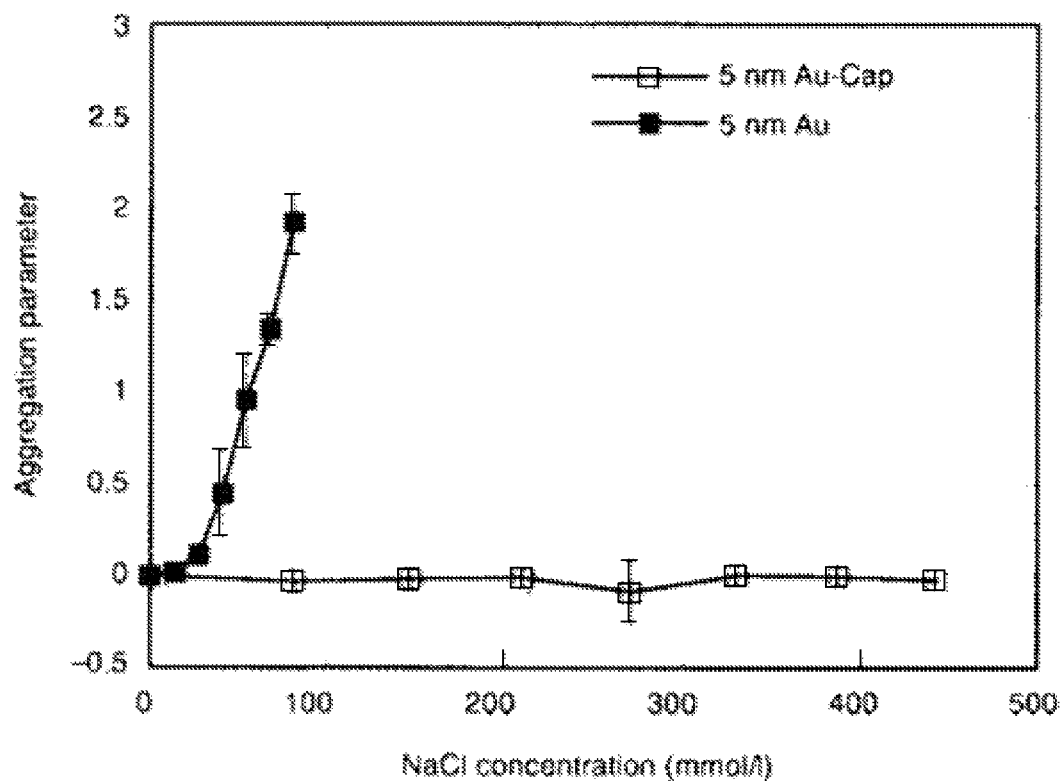
Figure 3A:
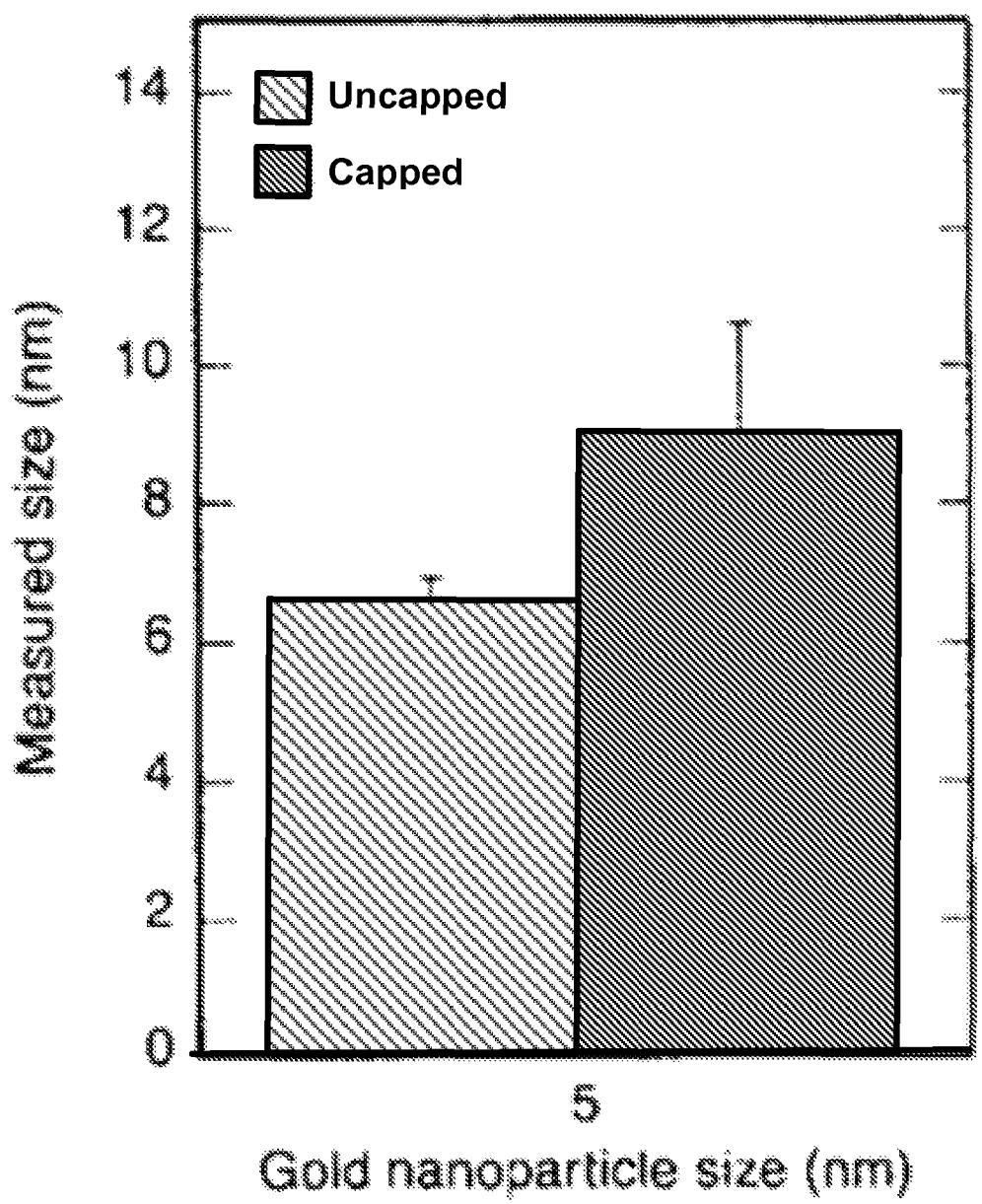
FIG. 3. Characterization of DNA/PEI and DNA/PEI-Au-Cap-RGD-ASA polyplexes. A. Mean size±SD (n=3) of 5 nm unmodified Au and Au-Cap measured using DLS. B. Ethidium Bromide competition assay for DNA/PEI polyplex formation. Plasmid DNA (26.6 μg/mL in TE buffer) and EtBr (1.1 μg/mL) was added to a fluorimeter vial to a final volume of 150 μl and read before and after the addition of each aliquot of PEI (0.5 μL, of 0.1 mg/mL). C. Size of DNA/PEI polyplexes modified with 5 nm Au-Cap-RGD nanoparticles were measured using DLS for low (13.3 μg DNA/mL) and high concentration (40 μg DNA/mL). D. Electron micrographs of negatively stained DNA/PEI polyplexes-Au. All the polyplexes were observed to contain Au particles. Scale bars are 100 nm. E. Number distribution of the amount of Au nanoparticles per surface area of polyplex (n=17).

The effect of clustered Arg-Gly-Asp (RGD) ligands on the transfection efficiency of DNA/PEI polyplexes was investigated using the penton base of Adenovirus type 2 as a design guide (FIG. 1). The penton base protein is approximately 16 nm in diameter and has a RGD to RGD distance of 5.7 nm [9]. To achieve a similar size and RGD to RGD distance for the RGD nanoclusters, stable RGD modified gold nanoparticles (Au-Cap-RGD, RGD nanoclusters) and stabilized gold nanoparticles (Au-Cap) were synthesized through the modification of 5 nm gold nanopaticles with the self-assembling peptides CCVVVT (Cap) (SEQ ID NO:1), CCVVVT-RGD (Cap-RGD) (SEQ ID NO:2), CCVVVT-RGD-Azidosalicylic Acid (Cap-RGD-ASA) (SEQ ID NO:3), and CCVVVT-ASA (Cap-ASA) (SEQ ID NO:4) via thiol/gold chemisorption. The Cap peptide was chosen for its ability to prevent gold nanoparticle aggregation in salt containing solutions (FIG. 2) [30]. Gold nanoparticles were stabilized through the formation of a peptide monolayer protected cluster (MPC) using a β-strand forming peptide, which resulted in stable particles in high salt solutions. Gold nanoparticle modification with the self-assembling peptides to form MPCs was confirmed through absorbance scans and dynamic light scattering DLS. Using an absorption scan, the Au-Cap nanoparticles were shown to be stable in up to 500 mM NaCl compared to only 15 mM for unmodified of the gold nanoparticles (FIG. 2). The size of the gold nanoparticles increased by approximately 4 nm after Cap peptide modification as expected based on the length of the peptide (FIG. 3A). To introduce bioactivity into the Au nanoparticles, MPC were formed with mixtures of Cap and Cap-RGD peptides and subjected to amino acid analysis to determine if the ratio of peptides used in solution was conserved after attachment (Table 1). The ratio on the surface for 99:1 and 90:10 Cap to Cap-RGD modified 20 nm nanoparticles were found to closely resembled the solution mixture as expected. However, when increased to 80:20, the ratio found on the surface was 89.8:10.2, suggesting that Cap-RGD peptides could only be packed efficiently up to 90 to 10 concentration ratio.

TABLE 1

RGD to RGD distance approximation for 5 nm Au-Cap-RGD

| Solution ratio | | Surface ratio[a] for 20 nm particles | | RGD to RGD distance for a 5 nm |
|---|---|---|---|---|
| % Cap | % Cap-RGD | % Cap | % Cap-RGD | particle |
| 99 | 1 | 97.2 | 2.8 ± 0.2 | 8.67-9.32 nm |
| 90 | 10 | 91.6 | 8.4 ± 1.0 | 4.9-5.52 nm |
| 80 | 20 | 89.8 | 10.2 ± 4.7 | 3.9-6.4 nm |

[a]Determined through amino acid analysis.

DNA/PEI-Au-Cap-RGD Polyplex Characterization

Figure 3B:
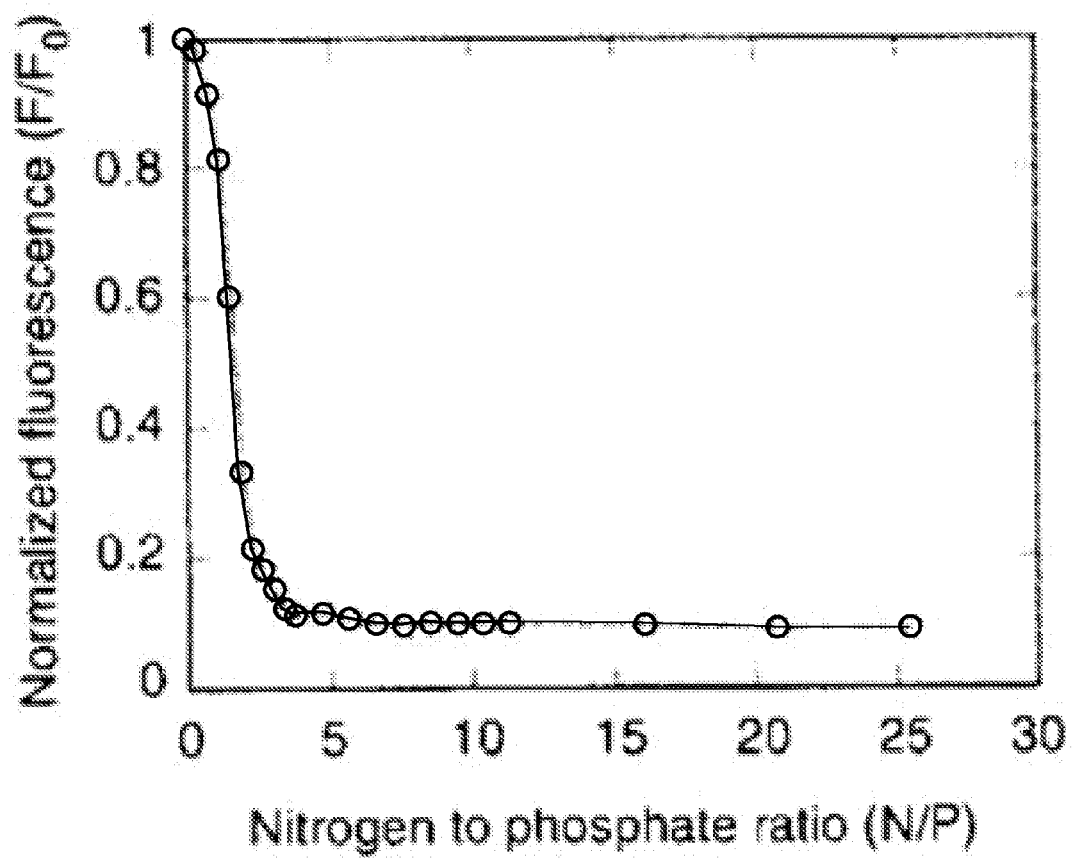
Figure 3C:
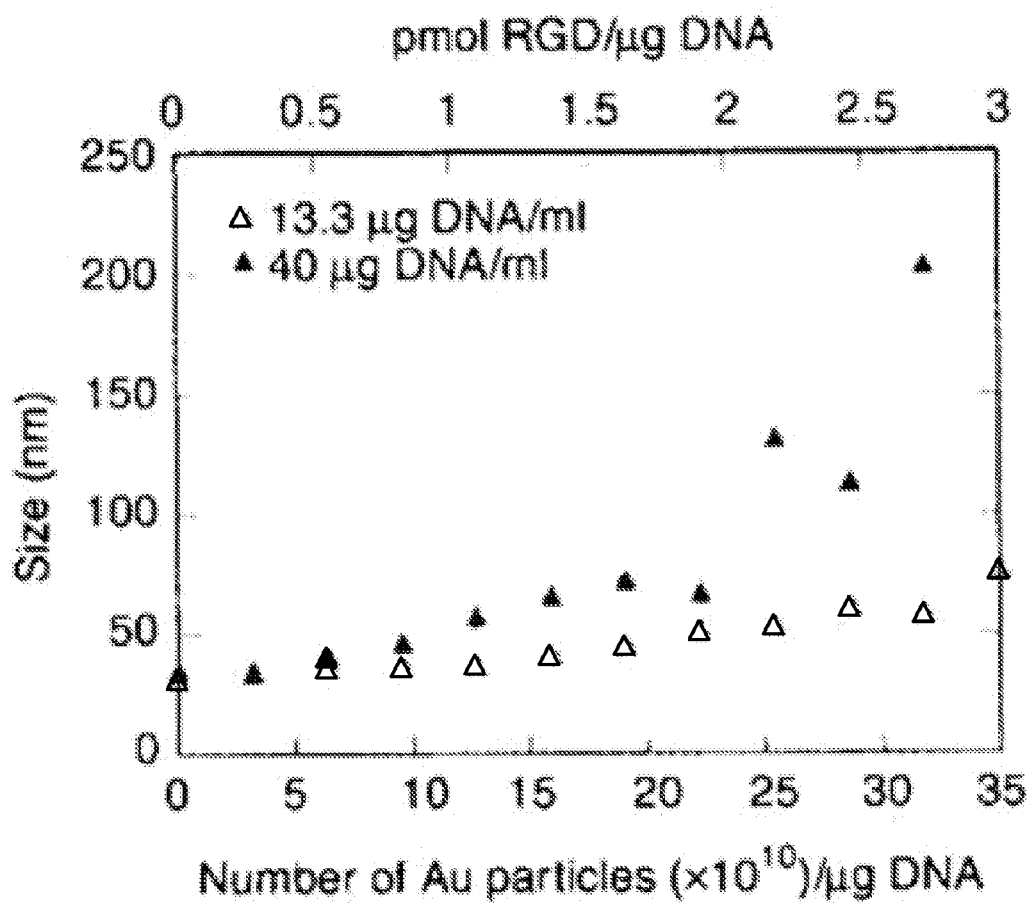
Figure 3D:
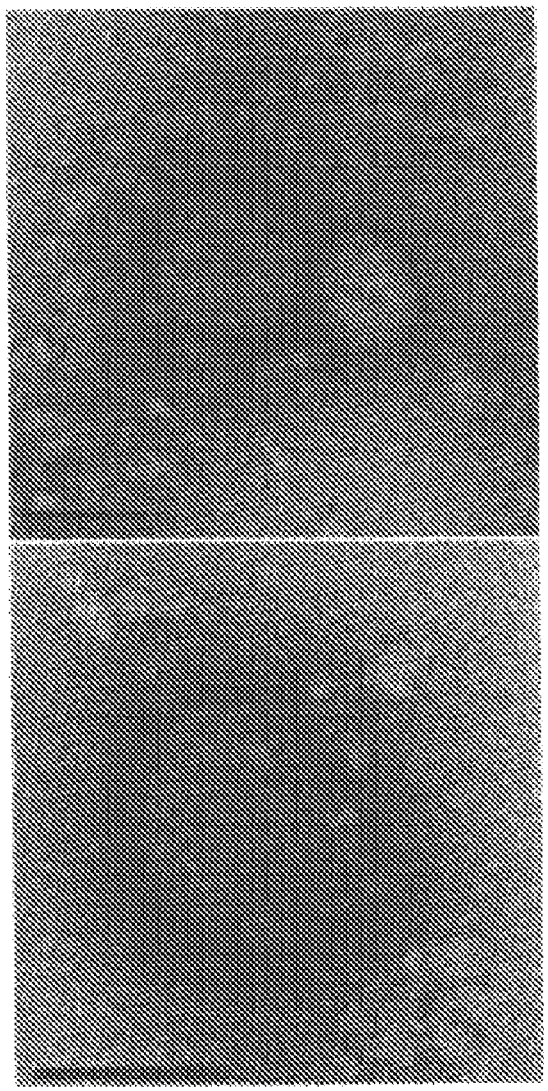
Figure 3E:
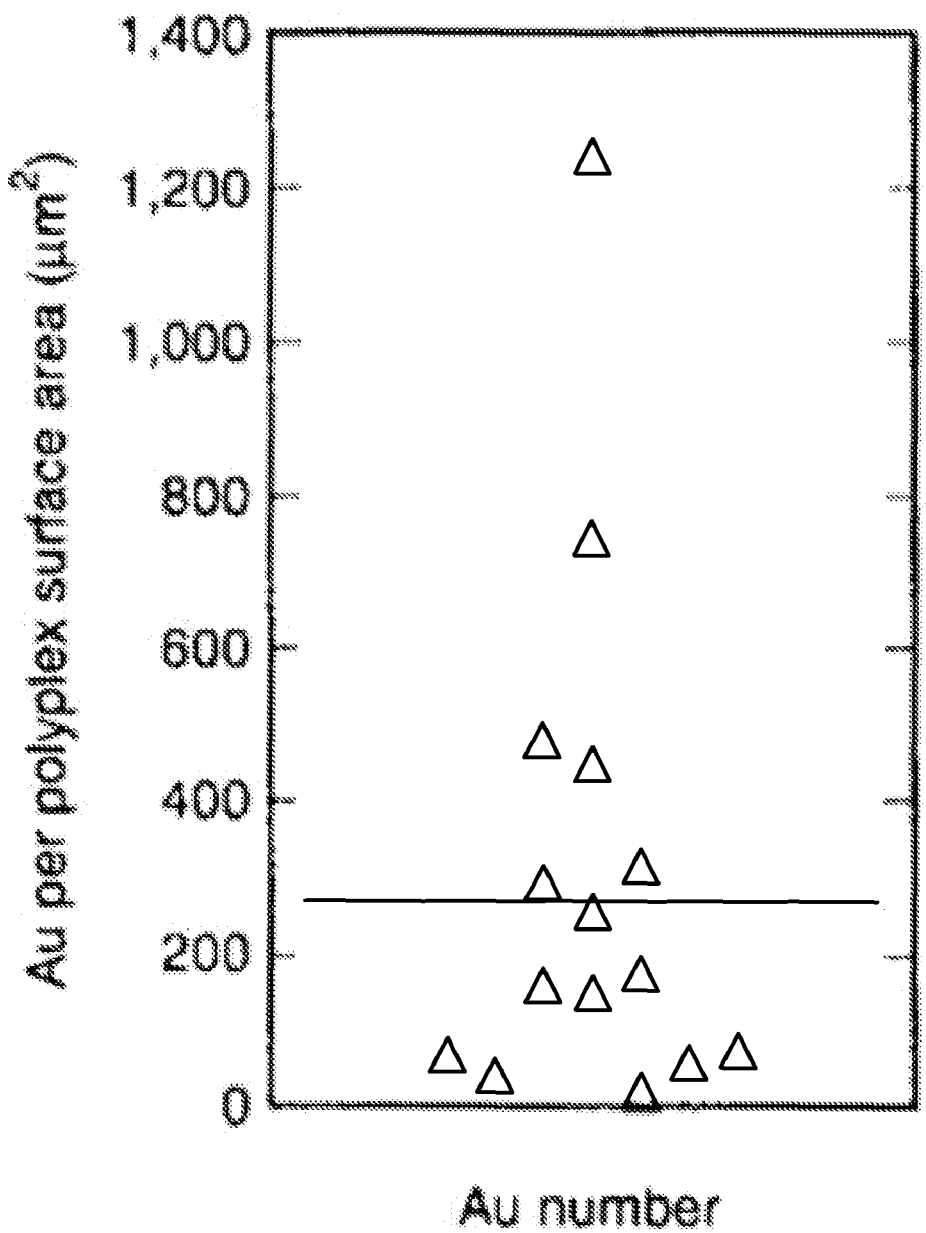

To determine the nitrogen to phosphate ratio (N/P) that resulted in compacted particles at the lowest N/P ratio, an ethidium bromide (EtBr) exclusion assay was used where the amount of EtBr release is quantified as the polyplex forms. At an N/P ratio of 5, the EtBr exclusion curve (FIG. 3b) began to plateau indicating full DNA/PEI complexation had been reached. Au-RGD-ASA nanoparticles were attached to DNA/PEI polyplexes (N/P of 10) using the photoreactive group ASA (FIG. 1C), which reacts with amines when exposed to UV light. The sizes and degree of modification of the resulting DNA/PEI-Au-RGD polyplexes were measured as a function of Au-RGD-ASA nanoparticle concentration using DLS and visualized through transmission electron micrographs (TEM). The size increased as Au-RGD-ASA nanoparticles were added for polyplexes formed with low (13.3 μg/mL) and high (40 μg/mL) DNA concentrations. Low concentration polyplexes showed a gradual increase in size from 32 nm to 76 nm for 0 to 35×1010 gold nanoparticles/μg DNA (FIG. 3C). High concentration polyplexes showed a gradual increase in size from 35 nm to 72 nm for 0 to 22×1010 nanoparticles/μg DNA. However, when higher amounts of Au-RGD-ASA nanoparticles were added (22 to 31×1010 nanoparticles/μg DNA) the size of the polyplexes increased from 72 nm to 203 nm (FIG. 3C). Transmission electron micrographs of negatively stained DNA/PEI-Au-RGD polyplexes showed similar size distribution results to the DLS (FIG. 3D). A maximum of 49 clusters of Au nanoparticles were observed in one polyplex structure. A distribution of polyplexes was seen containing different amounts of Au nanoparticles (FIG. 3E) with an average of 262 nanoparticles/μm2 of polyplex surface area (~10 Au nanoparticles/polyplex). Gold nanoparticles were clearly visible, indicating attachment to the surface of the polyplex suggesting that the Au-RGD nanoclusters will be available for interaction with cell surface receptors. All polyplexes were observed to contain nanoparticles.

Toxicity of Modified Au and DNA/PEI-Au-Cap-RGD-ASA Conjugates

Figure 4:
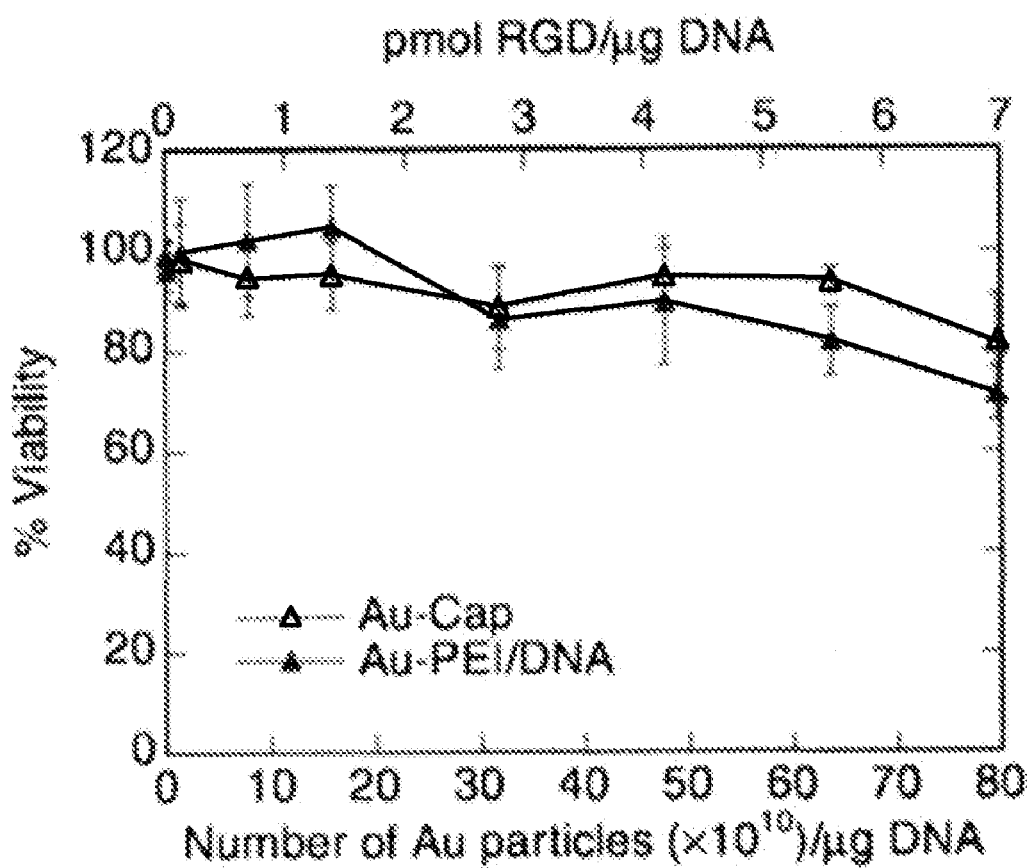
FIG. 4. Cell toxicity (proliferation) assay for Au-Cap nanoparticles and DNA/PEI-Au polyplexes. HeLa cells were plated in 96-well plates (7000 cells/well) for 12-hrs before exposing the cells to Au-Cap nanoparticles or DNA/PEI-Au-Cap-RGD-ASA polyplexes at varying concentrations of Au nanoparticles (1.7 μL/well) and testing for cell proliferation. The data was normalized to absorbance of untreated samples to calculate the percent viability for each sample (n=3).

To determine whether 5 nm Au-Cap or DNA/PEI polyplexes modified with 5 nm Au-RGD-ASA were toxic to cells, the proliferation rate of HeLa cells exposed to Au-Cap or DNA/PEI-Au-RGD-ASA was compared to that of untreated cells (FIG. 4). Au-Cap nanoparticles were not toxic to cells for all the concentrations tested up to $17.9 \times 10^{10}$ particles/well (equivalent to $80 \times 10^{10}$ particles/m DNA). DNA/PEI polyplexes were conjugated with increasing amounts of Au-RGD-ASA (0.224 µg DNA/well) and it was observed that the addition of nanoparticles did not increase the toxicity of polyplexes for all concentrations tested except at the highest concentration of particles ($80 \times 10^{10}$ particles/µg DNA), where the proliferation rate decreased to 72%.

Effects of Ligand Nanoclusters on HeLa Cells

Figure 8A:
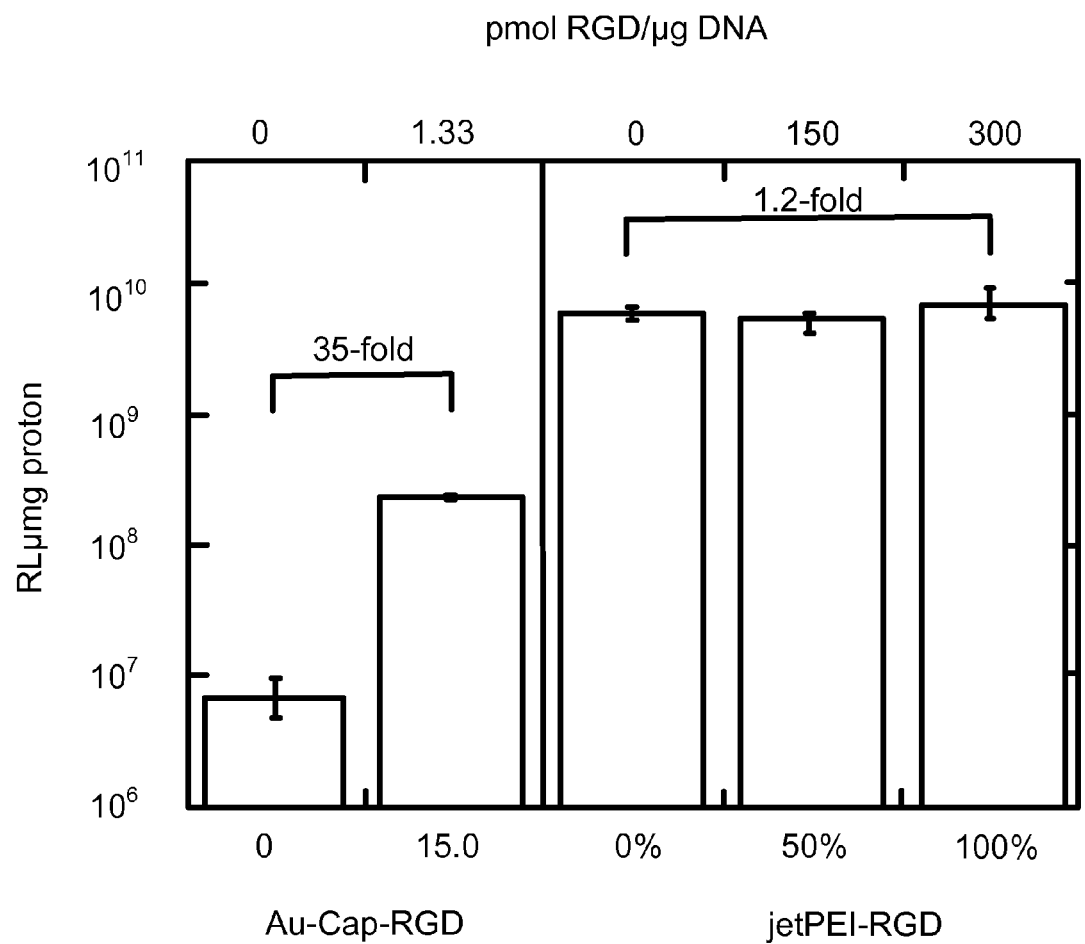
FIG. 8. Gene transfer to HeLa cells by RGD nanocluster modified polyplexes. A-B. Flow cytometry of HeLa cells passaged through scrapping (A) or trypsin (B). C-D. Gene transfer to HeLa$_{high}$ versus HeLa$_{low}$ using RGD nanocluster modified polyplexes (C) or jetPEI-RGD (D). E. Gene transfer in the presence of free RGD peptide. F. Gene transfer to HeLa$_{high}$ using polyplexes modified with RGD nanoclusters with different RGD to RGD distances.
Figure 8B:
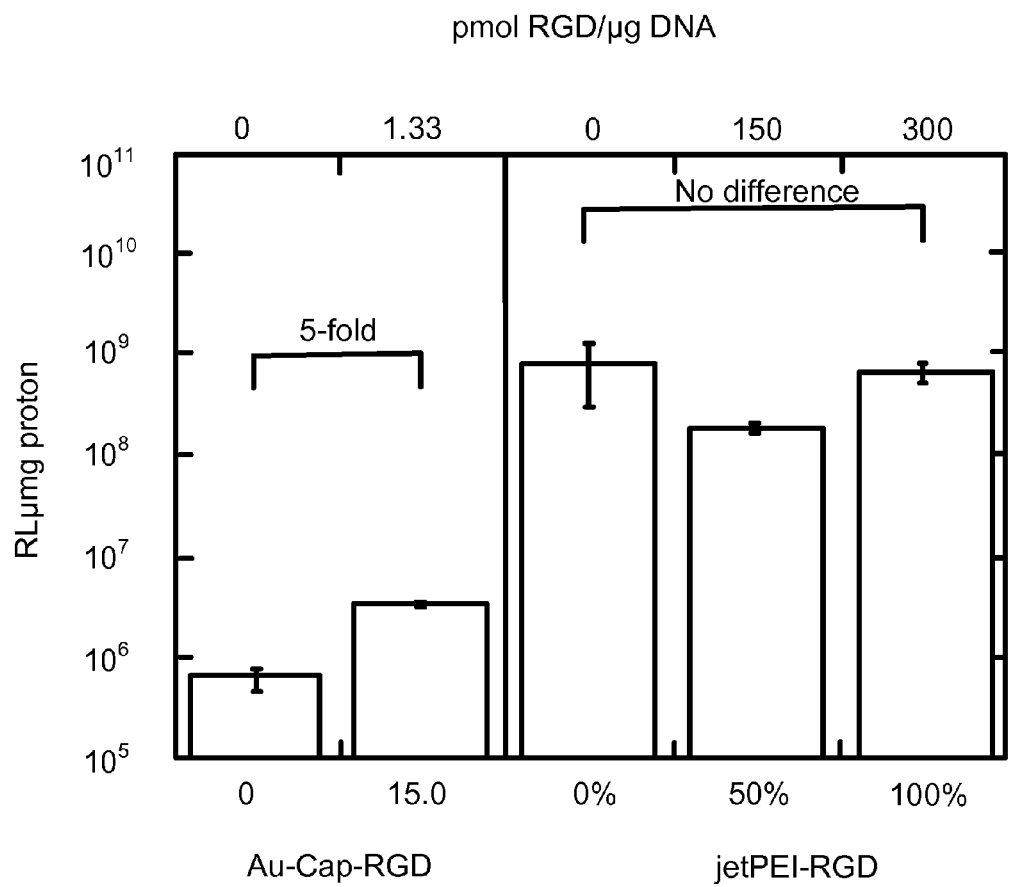

To generate HeLa cells with high and low $\alpha_v\beta_3$ integrin density, HeLa cells were passaged using trypsin or scrapping. The $\alpha_v\beta_3$ integrin expression profile of HeLa cells was determined using flow cytometry 12-hrs after plating (FIG. 5A; FIG. 8A-B). Cells that were detached via scrapping resulted in significantly (p<0.01) higher densities of $\alpha_v\beta_3$ integrins on the cell surface than cells detached using trypsin. These cells will be referred to as high $\alpha_v\beta_3$ density and low $\alpha_v\beta_3$ density for the scrapped and trypsinized cells respectively.

Figure 5B:
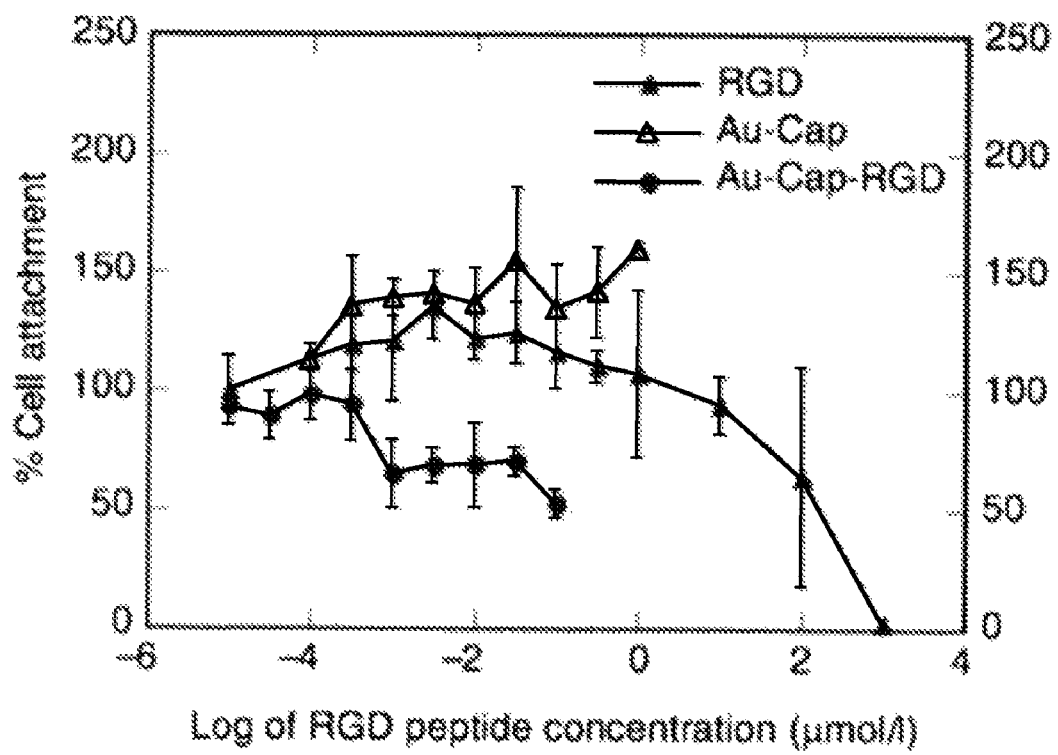

To determine the effectiveness of the RGD nanoclusters to bind to $\alpha_v\beta_3$ integrins, an anti-adhesion assay was used (FIG. 5B). The $IC_{50}$ concentration at which 50% of cell adhesion is inhibited for free RGD peptide was $\sim 10^2$ µM, which is comparable to that previously observed by others [18]. In contrast, Au-RGD nanoclusters required an equivalent RGD peptide of $\sim 10^{-1}$ µM to achieve the $IC_{50}$ level. Au-Cap did not affect cell attachment, indicating that the gold nanoparticle was not responsible for the observed results. These results suggest that synthesized RGD nanoclusters are able to bind to multiple integrin receptors simultaneously.

Example 2

In Vitro Targeting Using Ligand Nanoclusters

Transfection Using RGD Nanoclusters Conjugated to DNA/PEI Polyplexes

Figure 6A:
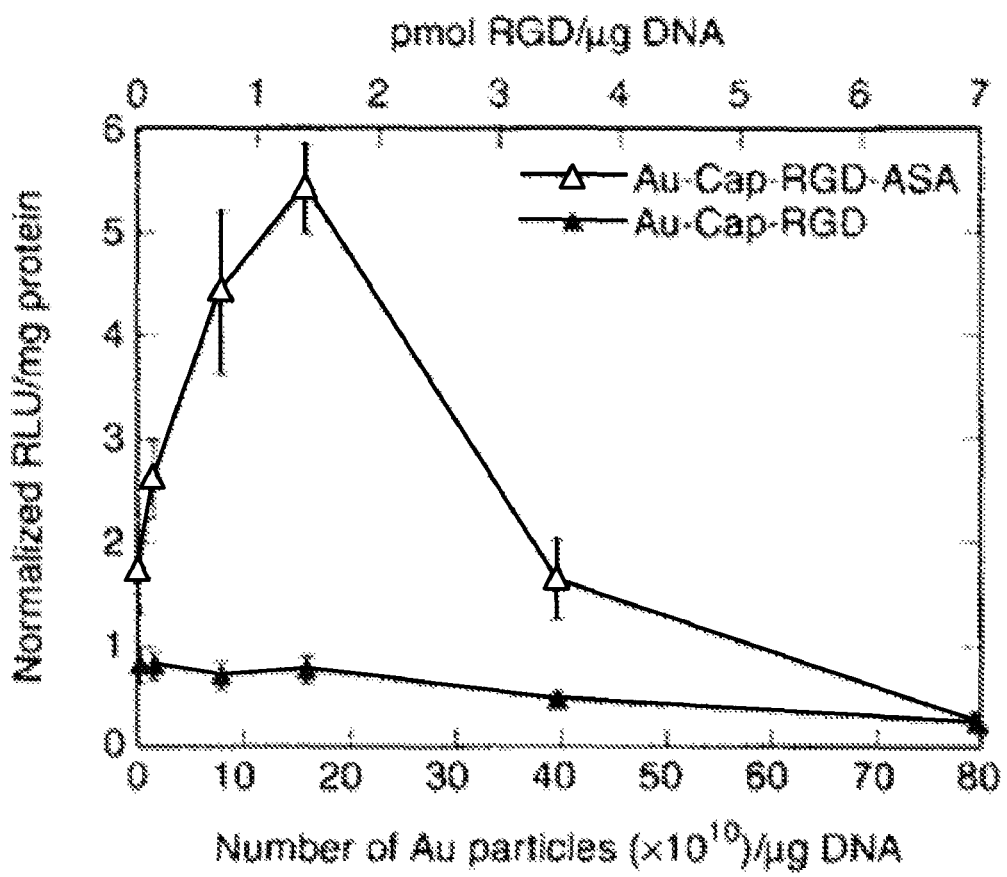
FIG. 6. Transfection efficiency in high and low $\alpha_v\beta_3$ integrin expressing HeLa cells measured using a luciferase reporter gene. A. Luciferase expression in low $\alpha_v\beta_3$ integrin expressing HeLa cells transfected with DNA/PEI-Au-Cap-RGD-ASA (with covalent linker) and DNA/PEI-Au-Cap-RGD (without covalent linker) (n=3). B. Luciferase expression in high $\alpha_v\beta_3$ integrin expressing HeLa cells transfected with DNA/PEI-Au-Cap-RGD-ASA (with covalent linker), DNA/PEI-Au-Cap-RGD (without covalent linker), and DNA/PEI-Au-Cap (n=3). The symbol * represents statistical significance to the level of p<0.001 for DNA/PEI-Au-Cap-RGD-ASA compared to DNA/PEI-Au-Cap-RGD and DNA/PEI-Au-Cap using the Tukey test. C. Luciferase expression in high $\alpha_v\beta_3$ integrin expressing HeLa cells transfected with DNA/PEI-Au-Cap-RGD-ASA (with covalent linker), DNA/PEI-Au-Cap-ASA (with covalent linker but no RGD), DNA/PEI-Au-Cap-RGD (without covalent linker), and DNA/PEI-Au-Cap (without covalent linker) (n=3). The symbol * represents statistical significance to the level of p<0.001 for DNA/PEI-Au-Cap-RGD-ASA compared to DNA/PEI-Au-Cap-RGD, DNA/PEI-Au-Cap, and DNA/PEI-Au-Cap-ASA using the Tukey test. D. Competitive binding of free RGD peptide for transfection of high $\alpha_v\beta_3$ integrin expressing HeLa cells with DNA/PEI-Au-Cap-RGD-ASA (n=3). The symbol * represents statistical significance to the level of p<0.05.
Figure 6B:
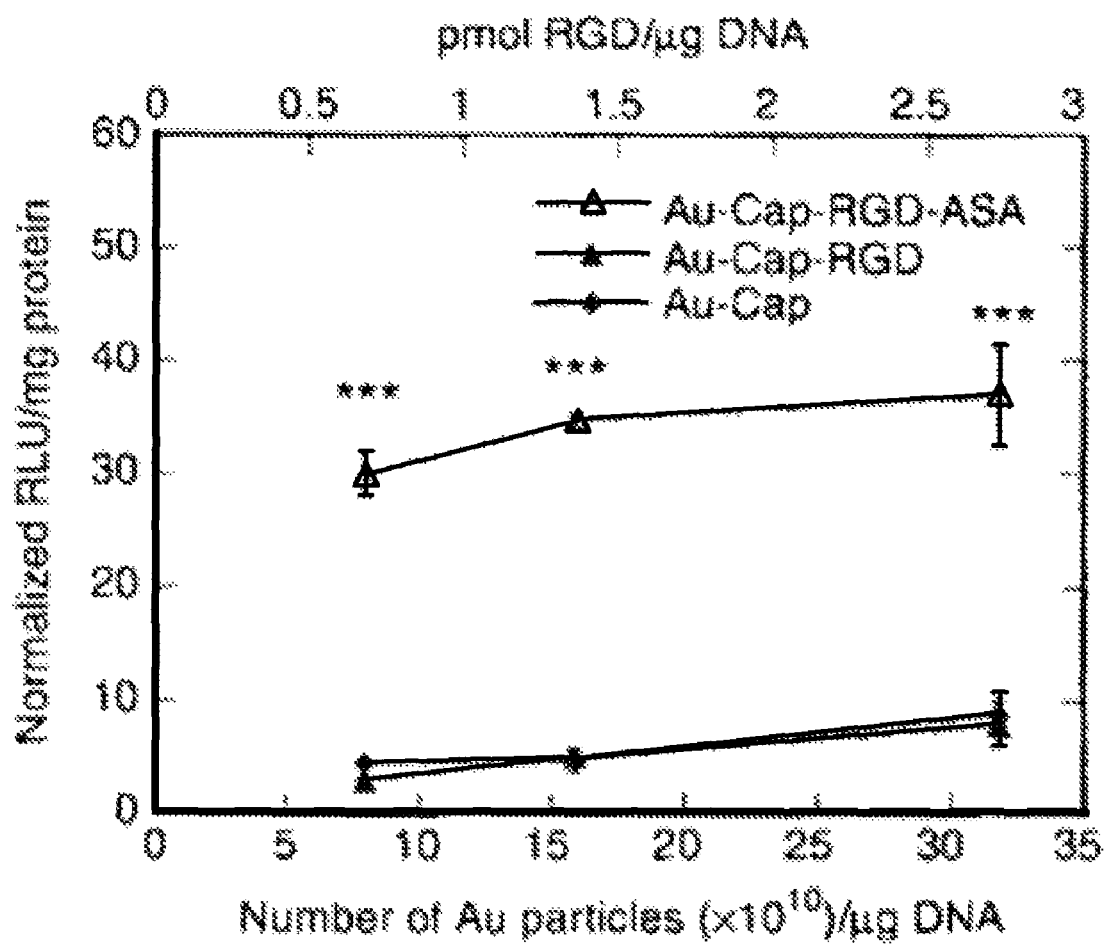
Figure 6C:
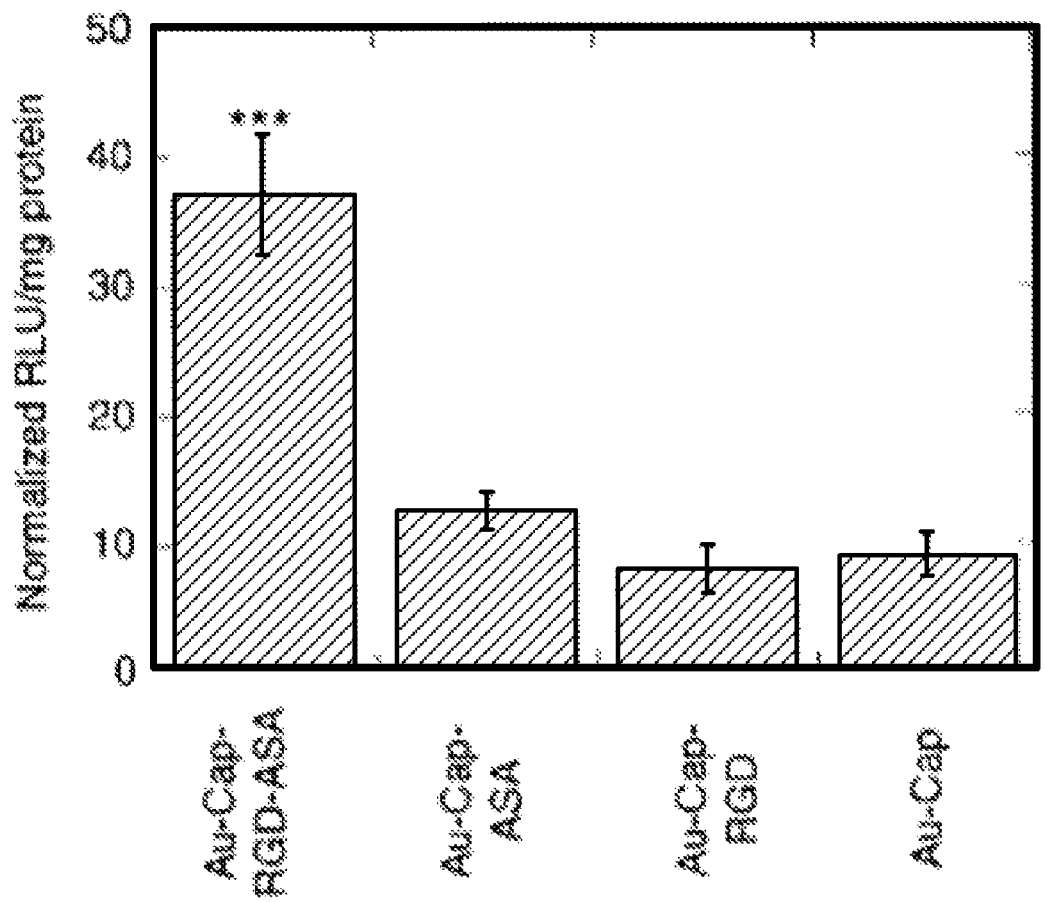

The effect of RGD nanoclusters on the transfection efficiency of DNA/PEI polyplexes was studied as a function of RGD nanoclusters bound to the polyplex and the density of integrins at the cell surface. DNA/PEI polyplexes were modified with RGD nanoclusters at concentrations ranging from $0.1 \times 10^{10}$ to $80 \times 10^{10}$ particles/µg DNA. For low $\alpha_v\beta_3$ density cells maximal expression was observed for $16 \times 10^{10}$ particles/µg DNA, showing a 5.4-fold increase in expression when compared to unmodified polyplexes (FIG. 6A). The effect of RGD nanoclusters on the transfection efficiency of DNA/PEI polyplexes to cells with high $\alpha_v\beta_3$ integrin density was studied with the range of RGD nanoclusters that resulted in the highest gene transfer for low $\alpha_v\beta_3$ density cells, $8 \times 10^{10}$ to $32 \times 10^{10}$ particles/µg DNA (FIG. 6B). Transfection of high $\alpha_v\beta_3$ density cells resulted in a 35-fold enhancement in transfection efficiency compared to unmodified polyplexes. As controls for the transfections in both low and high $\alpha_v\beta_3$ integrin density cells, polyplexes were mixed with Au-Cap-RGD nanoparticles that did not contain the ASA functional group and thus could not covalently bind to the polyplex. These transfections showed no increase in transgene expression for low $\alpha_v\beta_3$ integrin density cells and a 8-fold increase for high $\alpha_v\beta_3$ integrin density cells compared to unmodified polyplexes. To further investigate the 8-fold increase in transgene expression and to determine if the gold nanoparticles themselves were responsible for the observed enhancement in gene transfer, polyplexes were mixed with Au-Cap and Au-Cap-ASA ($16 \times 10^{10}$ particles/µg DNA). Transfections with Au-Cap and Au-Cap-ASA modified polyplexes resulted in an increase in transgene expression that was not statistically different from that observed for the Au-Cap-RGD (FIG. 6C).

Figure 6D:
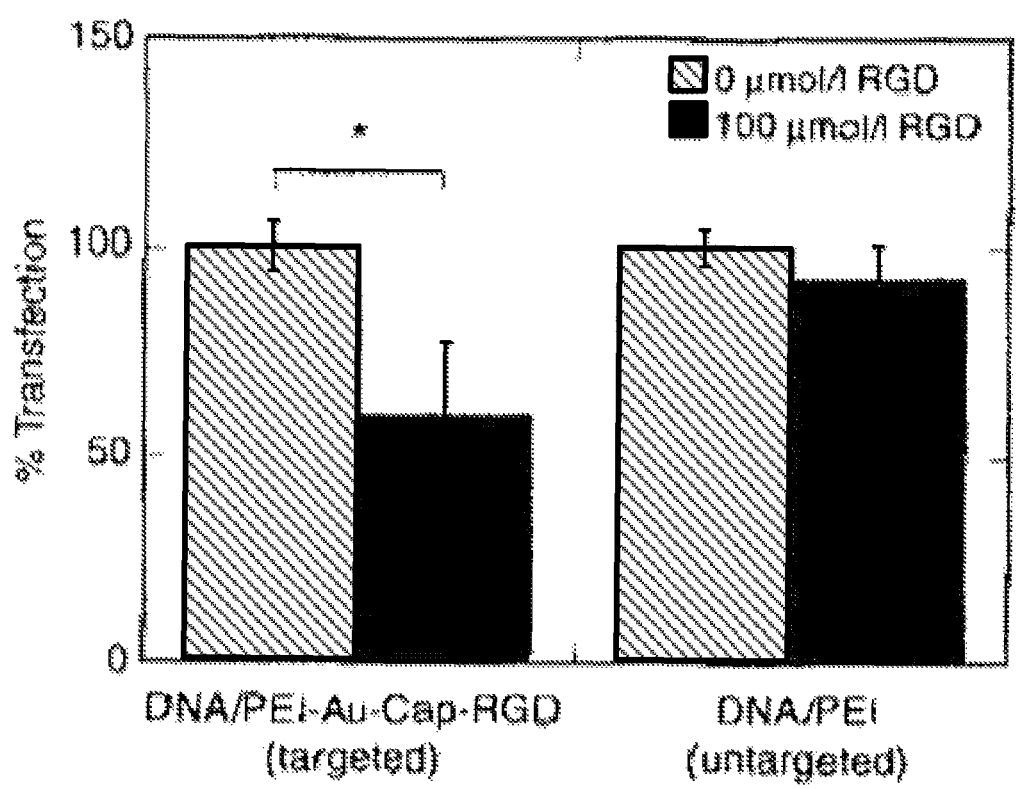

To ensure that the enhancement in gene transfer was due to the RGD nanoclusters binding to integrin receptors at the cell surface a competitive binding using free RGD peptide was conducted (FIG. 6D). DNA/PEI-Au-Cap-RGD-ASA polyplex gene transfer was decreased by 40% when free RGD peptide was added to the transfection mixture. The addition of free RGD peptide to untargeted polyplexes had no effect on gene transfer.

Figure 7A:
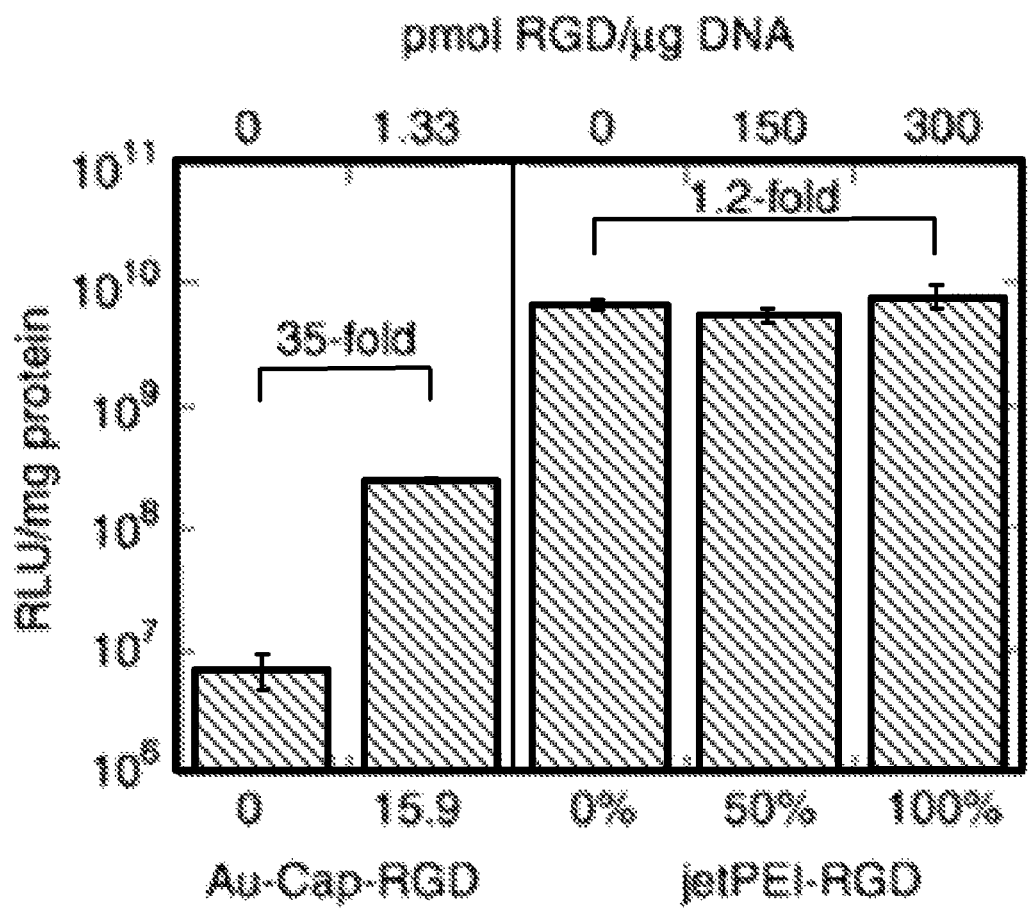
FIG. 7. Luciferase transgene expression of DNA/PEI and DNA/PEI-Au-Cap-RGD-ASA compared to DNA/jetPEI and DNA/jetPEI-RGD for (A) high and (B) low $\alpha_v\beta_3$ integrin expressing HeLa cells (n=3). Sensitivity of the vector to integrin density can be compared using the transfection efficiency of high and low integrin expressing cells by dividing the RLU/mg of the high expressing cells to the RLU/mg of the low expressing cells (Integrin Sensitivity Factor). C. Integrin Sensitivity Factor comparison of HeLa cells for DNA/PEI, DNA/PEI-Au-Cap-RGD-ASA, DNA/jetPEI, and DNA/jetPEI-RGD (n=3).
Figure 7B:
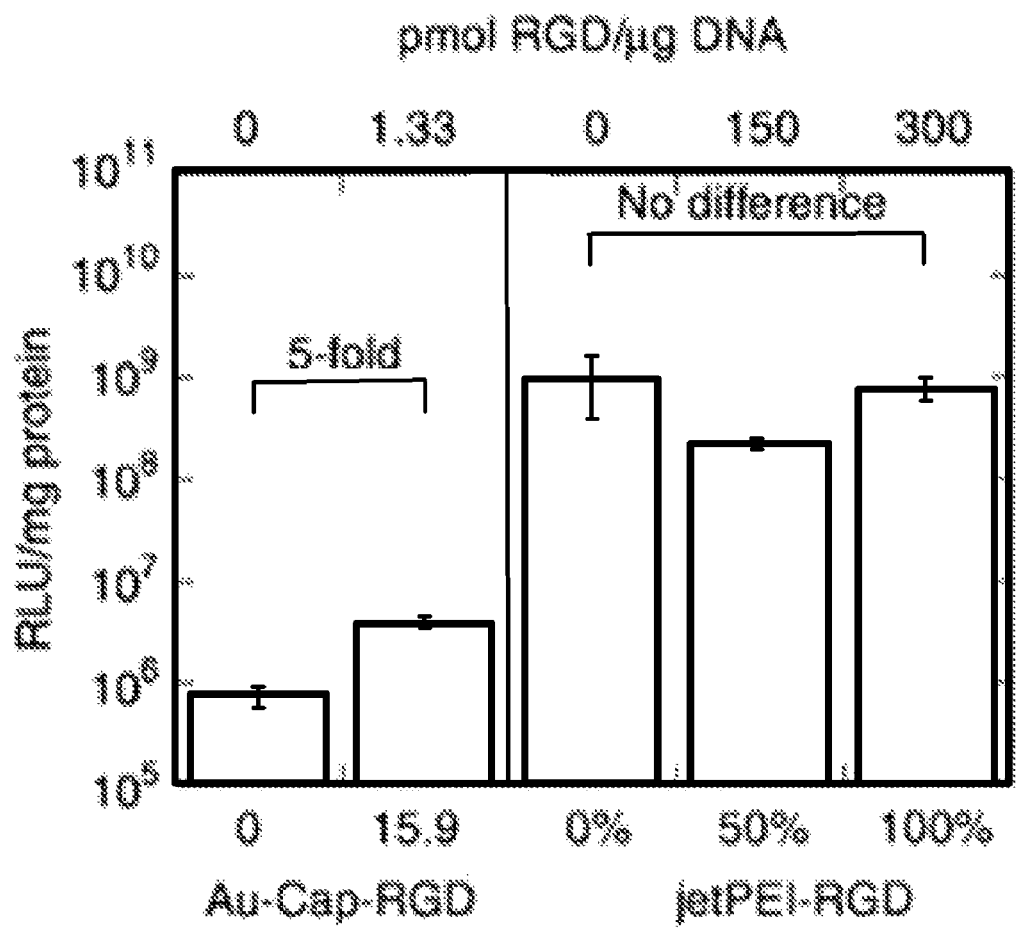
Figure 8C:
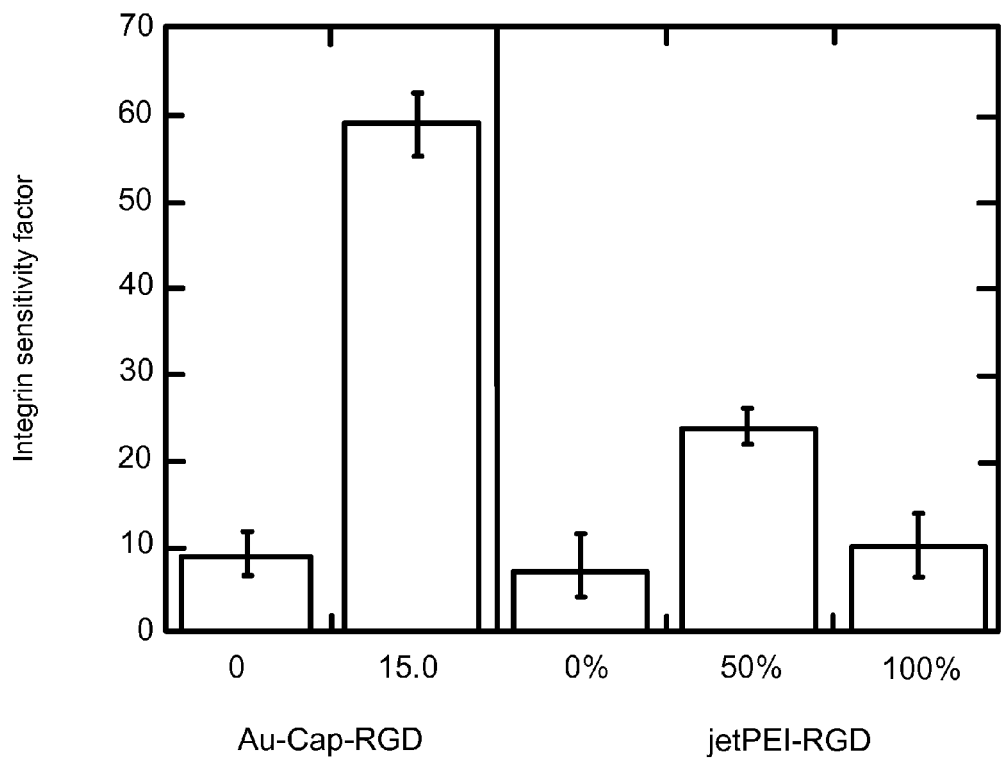
Figure 9A:
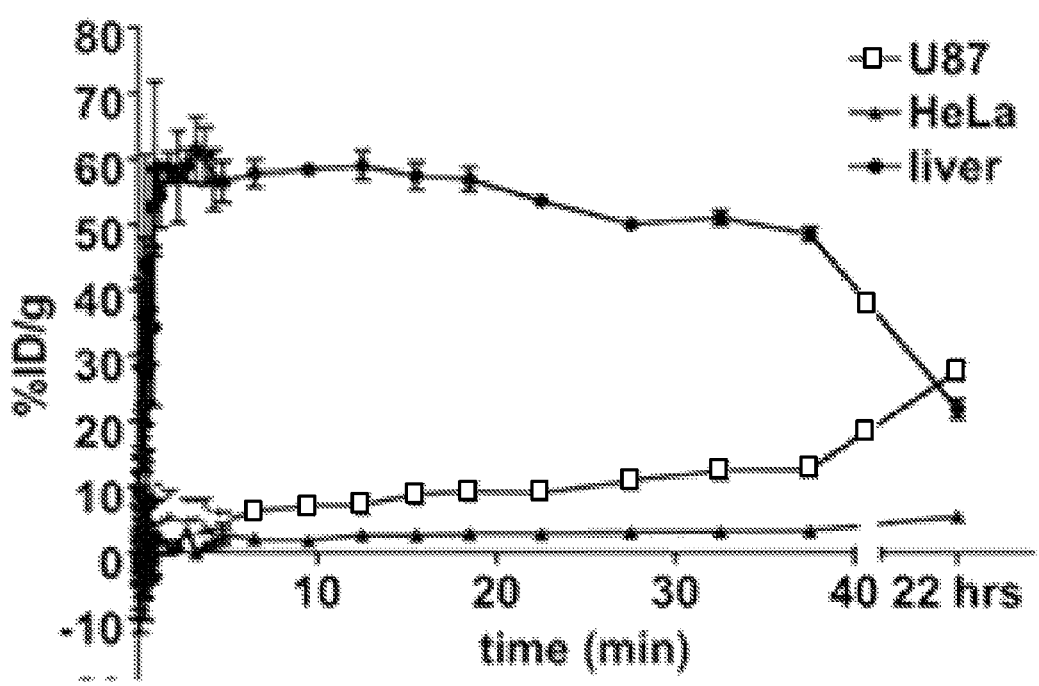
FIG. 9. Dynamic microPET scans. A, C. Dynamic microPET scans over 40 hours in the liver, U87 and HeLa cell tumors for RGD nanocluster targeted (A) and untargeted (C) polyplexes. B, D. MicroPET scan quantification at 22 hours for RGD nanocluster targeted (B) and untargeted (D) polyplexes in multiple organs. E-F. MicroPET/microCT scan images of the mice at 22 hours for targeted (E) and untargeted (F) polyplexes. n=3.
Figure 9B:
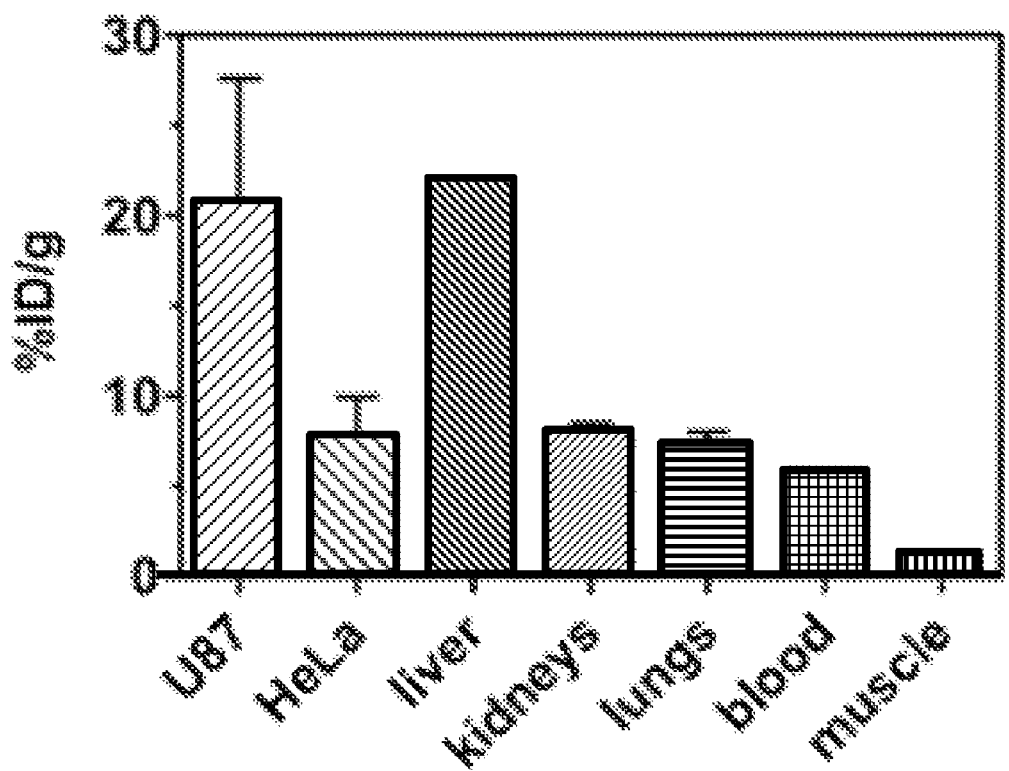
Figure 9C:
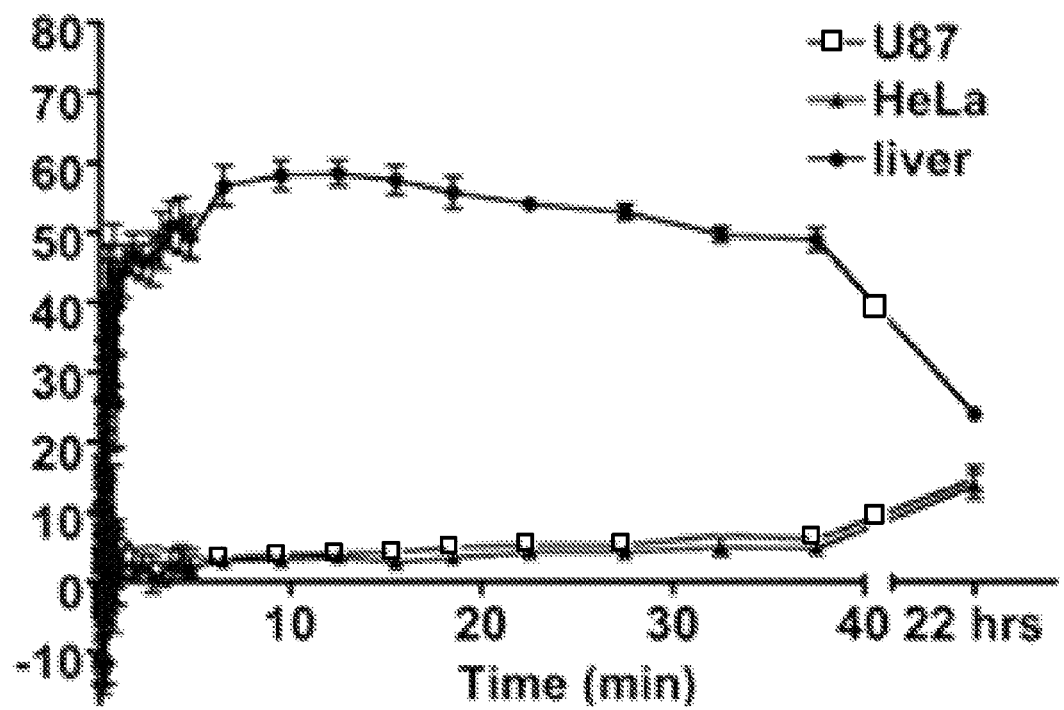
Figure 9D:
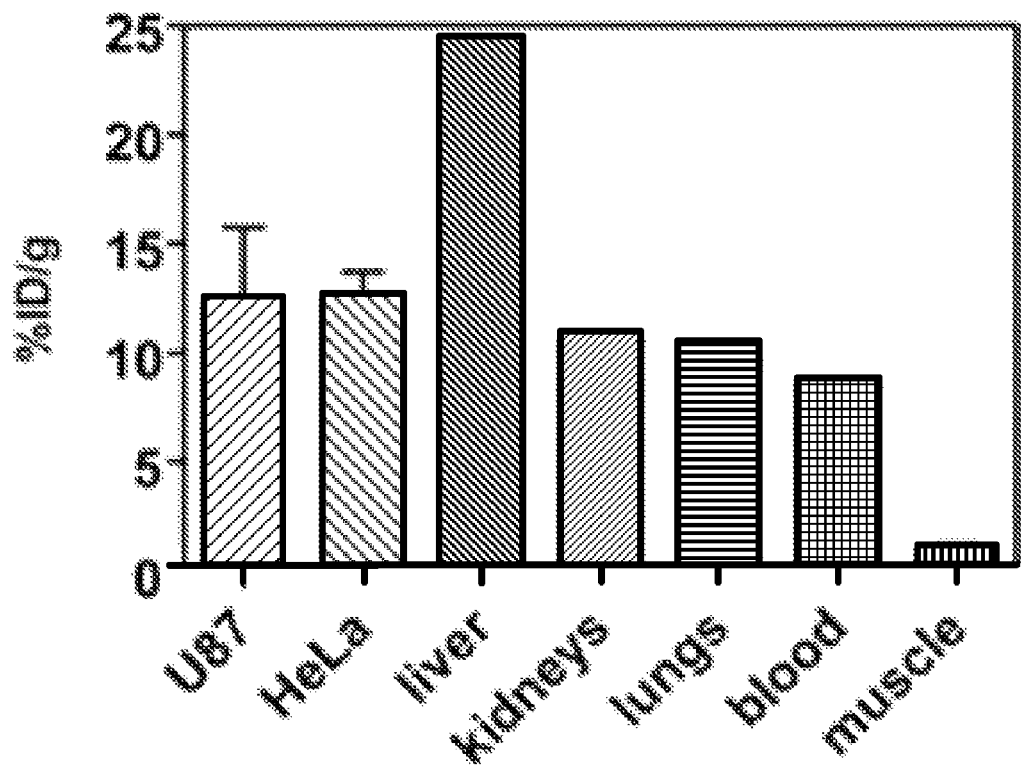
Figure 9E:
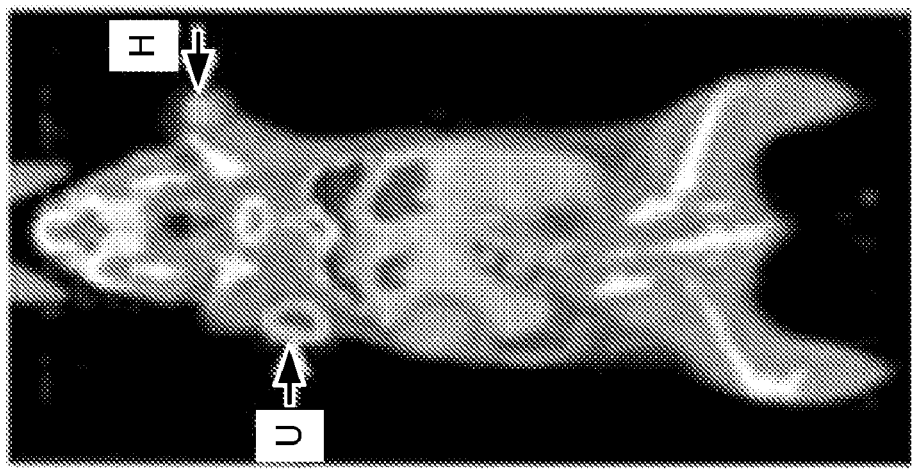
Figure 9F:
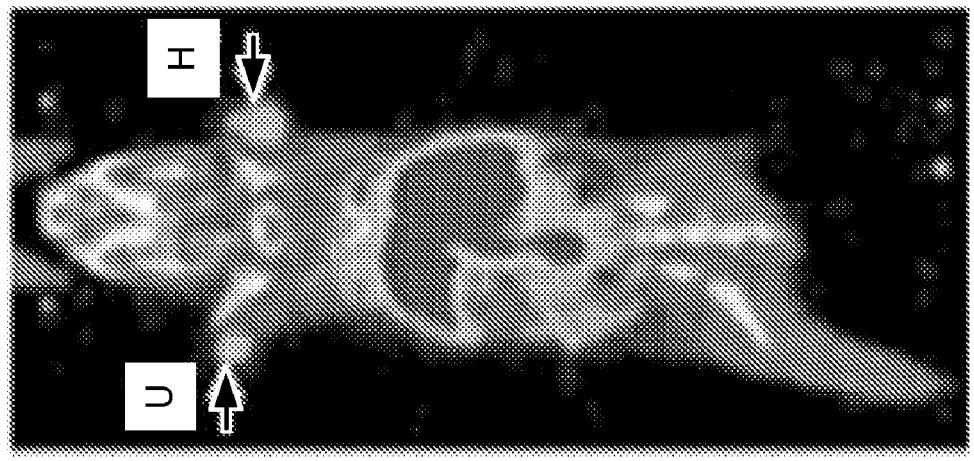

To test the effect of having clustered RGD peptide ligands on the surface of polyplexes compared to having homogenously distributed RGD peptide ligands on the surface of the polyplex, gene transfer experiments using RGD nanocluster modified polyplexes and jetPEI-RGD (a commercially available vector) were performed. High $\alpha_v\beta_3$ density cells were transfected with jetPEL jetPEI-RGD, or a 50:50 mixture (FIG. 7A). A 1.2-fold increase in transfection efficiency was observed when jetPEI-RGD was used compared to a 35-fold increase when RGD nanocluster modified polyplexes were used (FIG. 7A). Transfection of low $\alpha_v\beta_3$ density cells resulted in a 5.4-fold increase in expression for polyplexes modified with RGD nanoclusters, but no increase for jetPEI-RGD was observed (FIG. 7B). Looking at transfection efficiency as a function of integrin receptor density, RGD nanocluster modified polyplexes were able to transfect HeLa cells with high $\alpha_v\beta_3$ integrin receptor density (HeLa$_{high}$) 7-fold more efficiently than HeLa cells with low $\alpha_v\beta_3$ integrin receptor density (HeLa$_{low}$) and 35-fold more efficiently than unmodified polyplexes (FIG. 8C). In contrast, jetPEI-RGD polyplexes were able to transfect HeLa$_{high}$ cells only 1.5-fold more efficiently than HeLa$_{low}$ cells and 1.2-fold more efficiently than jetPEI without RGD (FIG. 8D). These results suggest that differences in gene transfer efficiency for vectors that contain clustered RGD ligands from those that contain homogeneous RGD ligands.

Figure 7C:
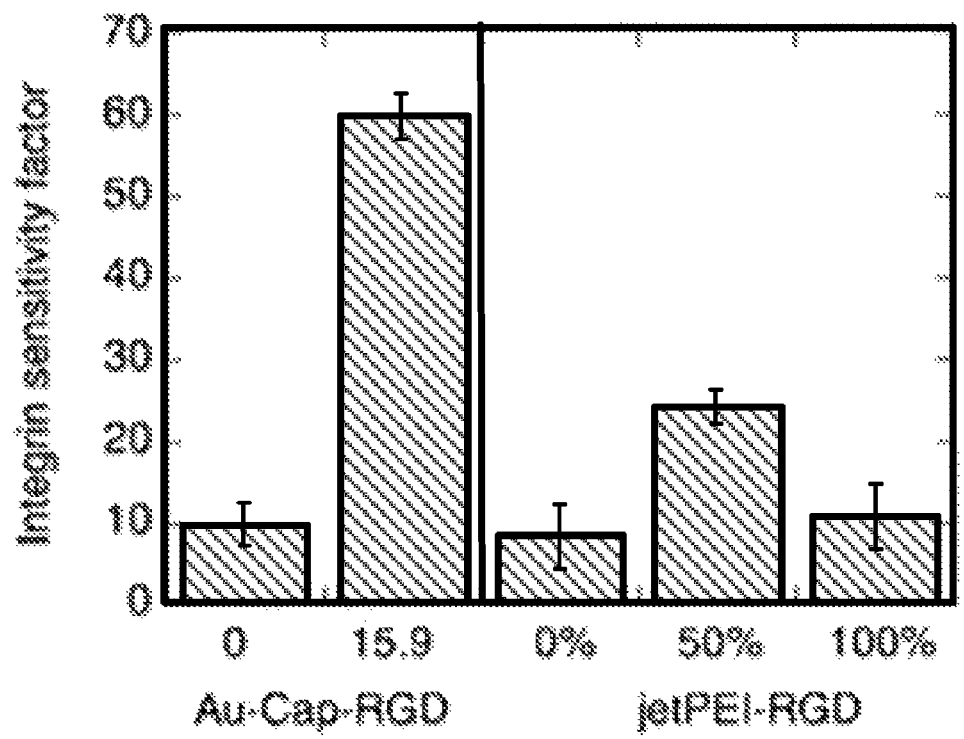

To further compare the results obtained for the low and high $\alpha_v\beta_3$ density cells, we defined an Integrin Sensitivity Factor (ISF), a ratio of the transfection level achieved with high and low $\alpha_v\beta_3$ density cells (FIG. 7C). Data from FIGS. 7A and 7B are used to generate FIG. 7C. An ISF value of 60 for RGD nanoclusters modified polyplexes was observed whereas for jetPEI-RGD the ISF was at most 20. Interestingly, cell trypsinization resulted in lower transgene expression for all of the vectors tested by at least an order of magnitude even for untargeted polyplexes. This indicates that the presence of clustered RGD ligands on the polyplex surface renders the delivery vector more sensitive to the density of receptors at the cell surface and that the local arrangement of RGD ligands on the surface of the polyplex is an important design characteristic for targeting.

RGD to RGD Distance of RGD Nanoclusters Affects the Efficiency of Gene Transfer of RGD Nanocluster Modified Polyplexes.

To test whether the distance between RGDs affects the transfection efficiency of RGD nanocluster modified polyplexes to HeLa$_{high}$ cells, 5 and 10 nm core gold nanoparticles were modified with 15 RGD peptides per particle, which results in RGD to RGD distances of 4.8 and 7.0 nm respectively. The same total amount of RGD per µg of DNA was used for each condition, so that the only difference between the polyplexes was the RGD to RGD distance. We found that gene transfer to HeLa$_{high}$ cells was more efficient when polyplexes were modified with RGD nanoclusters that had an RGD to RGD distance of 7 nm compared those modified with 4.8 nm RGD to RGD distance (FIG. 8F).

Example 3

In Vivo Targeting Using Ligand Nanoclusters

The ability of DNA/PEI polyplexes-modified with RGD nanoclusters to target tumors that express high levels of $\alpha_v\beta_3$ integrin receptors was studied using xenografts of human tumors in immunodeficient mice (NOD/SCID) (FIG. 9). Cells with high (U87) and medium (HeLa) $\alpha_v\beta_3$ integrin density were used to test the ability of RGD nanocluster modified polyplexes to target tumors based on the tumor's $\alpha_v\beta_3$ integrin density. U87 and HeLa cell tumors were formed in the same animal by injecting matrigel suspended cells on the right and left shoulders of the mice. $^{64}$Cu-modified PEI was used to form DNA/PEI polyplexes, which were subsequently modified with RGD-nanoclusters. As an initial control polyplexes that did not contain RGD-nanoclusters were used as our no targeting control. Dynamic PET scans, taken for 40 minutes, immediately following injection show that both RGD nanoclusters modified and unmodified polyplexes localize to the liver immediately following injection (FIG. 9 A,C). However, for the polyplexes modified with RGD nanoclusters U87 tumor colocalization was observed beginning at 5 minutes and continued to increase through the 40 minute of dynamic PET imaging. The next day (22-hrs) static micro-PET scans were acquired, which showed a general decrease in localization to the liver and an increase in the localization to both tumors (last point in FIG. 9 A,C). The quantification of the 22-hour time point of microPET scans shows that for RGD nanocluster targeted polyplexes localization was enhanced to the U87 tumor (FIG. 9B), while untargeted particles, result in the same level of polyplexes colocalized with both U87 and HeLa cell tumors (FIG. 9D). FIGS. 9E-F show representative scans of mice at the 22-hour time point for targeted and untargeted polyplexes. This data, showing effective targeting of $\alpha_v\beta_3$ high-density tumors using clustered RGD peptide ligands, demonstrates that clustered ligands on carrier surfaces may effectively target high-receptor-density tumors in subjects.

Example 4

Materials and Methods

Materials

Plasmid DNA was purified from bacteria culture using Qiagen (Santa Clara, Calif., USA) reagents and stored in Tris-EDTA (TE) buffer solution at −20° C. The plasmid pEGFP-Luc was promoted from Promega (Mountain View, Calif.). All other reagents were purchased from Fisher (Chino, Calif.) unless specified.

Synthesis of Cap, Cap-RGD, Cap-RGD-ASA, and Cap-ASA Peptides

The peptides CCVVVT-COOH (Cap) (SEQ ID NO:1) and Ac-CCVVVTGRGDSPSSK-COOH (Cap-RGD) (SEQ ID NO:5) were purchased from Genscript Corporation at 98.5% and >95% purity respectively. Cap-RGD-ASA was synthesized by reaction of Cap-RGD peptide with N-Hydroxysuccinimidyl-4-azidosalicylic acid (NHS-ASA, Pierce, Rockford, IL). Cap-RGD peptide (1 µmol) was reacted with 1.5 mg of NHS-ASA in 10% DMSO/0.1 M carbonate buffer (pH 8.3) for 1 hour. The final solution was dialyzed in milliQ water and lyophilized. Cap-ASA was synthesized by acetylation of the N-terminus and reaction of Cap peptide with p-azidobenzoyl Hydrazide (ABH, Pierce, Rockford, IL). The photoreactive group on Cap-ASA is not exactly the same as the one present on Cap-RGD-ASA (varies by an extra OH group), but the chemistry they undergo is the same and, thus, they were given the same abreviation. Cap peptide (1 µmol) was dissolved in 6% DMSO in 0.1 M MES (pH 6.0) and 10 µL of 300 mM acetic anhydride in THF was added and vortexed for 3 min. Acetic anhydride addition was repeated twice. The solution was dialyzed in milliQ water and lyophilized. The lyophilized peptide was dissolved in 500 µL of 0.1 M MES (pH 6.0) and reacted with 0.2 mg EDC (Advanced ChemTech, Louisville, KY) and 0.3 mg NHS (Pierce, Rockford, IL) for 15 min. ABH was added to a final concentration of 5 mM and diluted to a final volume of 1 mL using PBS and reacted for 2 hrs. The solution was dialyzed in milliQ water and lyophilized.

Formation of Au-Cap-RGD Nanoparticles (RGD Nanoclusters)

Au-Cap-RGD nanoparticles of different degrees of RGD modification were formed using a mixture of Cap and Cap-RGD or Cap-RGD-ASA peptides to the desired ratio. A total of 200 nmol of peptide with varying mixtures of Cap peptide, dissolved in 6% DMSO/PBS, and Cap-RGD or Cap-RGD-ASA peptide dissolved in PBS was added to Au nanoparticles purchased from Ted Pella (Redding, Calif.) and was reacted for 24 hours. A 1/10 volume ratio of 10× phosphate buffer (PB, pH=7.4) was added and incubated for an additional 24 hours. Purification of Au-Cap was achieved through dialysis using a 8 k MWCO Float-a-lyzer (Spectrapor, Rancho Dominguez, Calif.) in PB (3 mM KCl, 8 mM NaHPO$_4$, 1 mM KH$_2$PO$_4$, pH=7.4). Concentration of the nanoparticles was achieved by dehydration using Spectra/Gel Absorbent (Spectrapor, Rancho Dominguez, Calif.). Quantization of the number of peptides per particle was determined using amino acid analysis at the UCLA Biopolymer Lab. The concentration of Valines was used to calculate the amount of total peptides (Cap and Cap-RGD) reacted with the Au nanoparticles. The concentration of Arginine was used to calculate the amount of Cap-RGD peptides. The ratio of Cap to Cap-RGD peptides was determined using the calculated values. The sizes of Au-Cap and uncapped nanoparticles were measured using DLS with a Malvern Zetasizer nano ZS.

RGD Spacing Determination

Distances between RGD peptides on a particle surface can be calculated using surface area of the particle and theoretical peptide length. Assuming 1.93 peptides/nm$^2$ [30], a 5 nm particle would contain 151 peptides. The theoretical distance of the RGD sequence from the surface (~2.7 nm) would increase effective particle diameter to 10.4 nm. Using the percent of Cap-RGD peptides to Cap peptides, we calculated the number of RGD peptides that would be present per particle. For example, for a 90:10 Cap to Cap-RGD we obtained 15 Cap-RGD peptides per particle which would equally share surface area of 23 nm$^2$. This resulted in a theoretically calculated spacing of ~5 nm between RGD peptides.

Salt Stability of Au-Cap

Peptide-modified (Au-Cap) and unmodified particles were tested to check their salt stability. Au and Au-Cap nanoparticles were added to semi-micro cuvettes and serial additions of NaCl solution were added every 15 min followed by a wavelength scan from 400-900 nm (Beckman DU 730, Fullerton, Calif.). Aggregation parameter (AP) used to quantify aggregation was calculated using the equation AP=(A−A$_0$)/A$_0$. A is the integral of absorbance from 600 to 700 nm, and A$_0$ is the integral of absorbance from 600 to 700 nm of the initial solution without salt added (see FIG. 2 area under the curve).

Size Characterization of DNA/PEI-Au Polyplexes

DNA/PEI polyplexes were formed by mixing equal volumes of plasmid DNA (4.4 µg) with 25 kDa branched PEI (1 mg/mL, Sigma, St. Louis, Mo.) to get an N/P of 10 in a final volume of 330 µL of milliQ water. PEI was added to the DNA solution, vortexed for 10 seconds, and incubated at room temperature for 15 minutes. Specified concentrations of Au-Cap, Au-Cap-RGD or Au-Cap-RGD-ASA nanoparticles (10 µL) were added to the DNA/PEI polyplexes and exposed to ambient light for 15 minutes. The optimal N/P ratio for DNA/PEI complexes was determined using an Ethidium bromide (EtBr) exclusion assay by measuring fluorescence using a Modulus 20/20 Fluorimeter/Luminometer (Turner Biosystems, Sunnyvale, Calif.). The size of DNA/PEI-Au-Cap-RGD-ASA polyplexes was determined using dynamic light scattering (DLS) and TEM. DNA/PEI polyplexes for DLS size measurements were formed at normal (13.3 µg DNA/mL) and high concentration (40 µg DNA/mL) at an N/P of 10. Normal concentration DNA/PEI polyplexes were formed as previously described. High concentration DNA/PEI polyplexes were formed as previously described in a final volume of 110 µL of milliQ water. Au-Cap-RGD-ASA nanoparticles were added (2 µL per increment, $7 \times 10^{13}$ particles/mL) to the DNA/PEI polyplexes, vortexed for 10 seconds, and incubated at room temperature for 2 minutes. Size readings were taken between each increment using a Malvern ZetaSizer nanoZS (Malvern Instruments, Worcestershire, UK). High concentration DNA/PEI polyplexes were formed for TEM measurements and Au-Cap-RGD-ASA nanoparticles were added (3.95 µL, $3.5 \times 10^{14}$ particles/mL), vortexed for 10 seconds, and incubated at room temperature for 15 min. A droplet of 3 µL DNA/PEI-Au-RGD solution was applied to a glow discharged continuous carbon film coated copper grid. The solution was suspended on the grid for 10 seconds before removing the excess liquid by blotting with Whatman filter paper. The grid was then washed twice with 5 µL of distilled water and incubated for 15 seconds with 2% uranyl-acetate solution for negative staining. The air dried grid was then observed with a JEM-1230 transmission electron microscope. The micrograph images were recorded under a magnification of 50,000 on a TIVPS 2 k×2 k CCD camera [50].

Integrin Quantification with Flow Cytometry

HeLa cells were detached either through scrapping or using 0.25% Trypsin-EDTA during passaging, plated on 6-well plates (200,000 cells/well), and incubated for 12-hrs. The cells were detached from the wells by scrapping and stained using Alexa488 conjugated anti-$\alpha_v\beta_3$ monoclonal antibody (MAb 23C6, Santa Cruz Biotechnology, Santa Cruz, Calif.) following the Santa Cruz Biotechnology flow cytometry protocol.

Antiadhesion Assay

HeLa cells (ATCC, Manassas, Va.) were cultured in DMEM medium (Invitrogen, Carlsbad, Calif.) supplemented with 10% Bovine Growth Serum (BGS, Hyclone, Logan, Utah). The cells were cultured at 37° C., with 98% humidity and 5% $CO_2$. Cells were regularly subcultured using trypsin. 96-well plates were coated with human vitronectin by incubating a vitronectin solution (50 µL of 3 µg/mL, Invitrogen, Carlsbad, Calif.) in the well for 12-hrs at 37° C. The wells were washed three times with PBS and blocked with BSA (50 µL of 2% BSA in PBS) for 30 minutes at 37° C. The wells were washed three times with PBS and 100 µL/well of serum-free DMEM was added before chilling on ice. HeLa cells were harvested by scrapping using cell scrapers (USA Scientific, Ocala, Fla.), pelleted, and resuspended in ice cold serum-free DMEM to 400,000 cells/mL. 200 µL of serum-free DMEM was added to 50 µL of Au-Cap-RGD solution and vortexed before 250 µL of cell solution was added to the cells and placed in ice for 15 minutes. 100 µL/well of cell solution was added and allowed to incubate at 37° C. for 50 minutes. The plate was submerged in PBS in a Ziploc bag and centrifuged upside down for 10 minutes at 250 g. The plate was washed gently with additional PBS and removed. Remaining liquid was removed from the wells. The cells were fixed using 4% paraformaldehyde solution for 15 minutes and washed 3 times with PBS. Crystal violet solution was added to each well and incubated for 1 hr. The wells were then washed with milliQ water until no crystal violet was visible in solution. Crystal violet was solubilized using 10% acetic acid plate for 15 min and the absorbance at 570 nm was taken using the PowerWave microplate reader (BioTek, Winooski, Vt.).

Bolus Transfection with Polyplexes

HeLa cells were transfected using DNA/PEI-Au-Cap-RGD-ASA polyplexes. HeLa cells were either removed with 0.25% Trypsin-EDTA or scrapped and then plated 40,000 cells/well in DMEM supplemented with 10% BGS (Hyclone, Logan, Utah) on a 24 well TC-plate (USA scientific, Ocala, Fla.). Cells were incubated for 12 hrs (50% confluency) at 37° C. and 5% $CO_2$. 1.33 µg of DNA from low concentration DNA/PEI-Au polyplex solution, formed as previously described, were added per well. Immediately following addition, 1.5 M NaCl solution was added to each well (10% of polyplex volume). JetPEI and jetPEI-RGD polyplexes were formed and added according to manufacturers protocols at an N/P of 5. Cells and polyplexes were allowed to incubate for 48 hrs. Cells were lysed and a luciferase assay was performed as described in the Promega luciferase assay kit and measured using a Luminometer (Turner Biosystems, Modulus 20/20, Sunnyvale, Calif.). Protein concentration was measured using the Bradford reagent, Coomassie Plus (Pierce, Rockford, Ill.), following manufactures protocols.

Bolus Transfection with RGD Competition

HeLa cells were transfected using DNA/PEI-Au-Cap-RGD-ASA polyplexes in the presence of RGD peptide in solution. Bolus transfection using DNA/PEI-Au-Cap-RGD-ASA and DNA/PEI polyplexes was performed similarly as described above except RGD peptide (Ac-GCGYGRGD-SPSSK-$NH_2$ (SEQ ID NO:6), Standford PAN, Palo Alto, Calif.) dissolved in PBS was added to each well to a final concentration of 100 µM and incubated at 37° C. for 15 min prior to addition of polyplexes. Cells and polyplexes were allowed to incubate for 4 hrs before replacing with fresh media and incubating for an additional 44 hrs. Cells were lysed and assayed as described previously.

Statistics

All statistical analyses were performed using the computer program Prism (GraphPad, San Diego, Calif.). experiments were statistically analyzed using a one-way analysis of variance using the Tukey test, which compares all pairs of columns, using a 95% confidence interval. When only two groups were compared, the Student t test was used as indicated in the figure legends.

References

1. Arnold, M., et al. (2004). Activation of integrin function by nanopatterned adhesive interfaces. *ChemPhysChem* 5: 383-388.

2. Koo, L. Y., Irvine, D. J., Mayes, A. M., Lauffenburger, D. A., and Griffith, L. G. (2002). Co-regulation of cell adhesion by nanoscale RGD organization and mechanical stimulus. *J. Cell Sci.* 115: 1423-1433.

3. Maheshwari, G., Brown, G., Lauffenburger, D. A., Wells, A., and Griffith, L. G. (2000). Cell adhesion and motility depend on nanoscale RGD clustering. *J. Cell Sci.* 113: 1677-1686.

4. Kong, H. J., Polte, T. R., Alsberg, E., and Mooney, D. J. (2005). FRET measurements of cell-traction forces and nanoscale clustering of adhesion ligands varied by substrate stiffness. *Proc. Natl. Acad. Sci. U.S.A.* 102: 4300-4305.

5. Kong, H. J., Hsiong, S., and Mooney, D. J. (2007). Nanoscale Cell Adhesion Ligand Presentation Regulates Nonviral Gene Delivery and Expression. *Nano Lett.* 7: 161-166.

6. Cavalcanti-Adam, E. A., Micoulet, A., Blummel, J., Auernheimer, J., Kessler, H., and Spatz, J. P. (2006). Lateral spacing of integrin ligands influences cell spreading and focal adhesion assembly. *Eur. J. Cell Biol.* 85: 219-224.

7. Hughes, P. E., and Pfaff, M. (1998). Integrin affinity modulation. *Trends Cell Biol.* 8: 359-364.

8. Humphries, M. J. (1996). Integrin activation: the link between ligand binding and signal transduction. *Curr. Opin. Cell Biol.* 8: 632-640.

9. Stewart, P. L., et al. (1997). Cryo-EM visualization of an exposed RGD epitope on adenovirus that escapes antibody neutralization. *EMBO J.* 16: 1189-1198.

10. Medina-Kauwe, L. K. (2003). Endocytosis of adenovirus and adenovirus capsid proteins. *Adv Drug Delivery Rev* 55: 1485-1496.

11. Chiu, C. Y., Mathias, P., Nemerow, G. R., and Stewart, P. L. (1999). Structure of Adenovirus Complexed with Its Internalization Receptor, alpha vbeta 5 Integrin. *J. Virol.* 73: 6759-6768.

12. Goldman, M. J., and Wilson, J. M. (1995). Expression of alpha v beta 5 integrin is necessary for efficient adenovirus-mediated gene transfer in the human airway. *J. Virol.* 69: 5951.

13. Mizuguchi, H., et al. (2002). CAR- or alpha v integrin-binding ablated adenovirus vectors, but not fiber-modified vectors containing RGD peptide, do not change the systemic gene transfer properties in mice. *Gene Ther.* 9: 769-776.

14. Mathias, P., Wickham, T., Moore, M., and Nemerow, G. (1994). Multiple adenovirus serotypes use alpha v integrins for infection. *J. Virol.* 68: 6811-6814.

15. Wickham, T. J., Mathias, P., Cheresh, D. A., and Nemerow, G. R. (1993). Integrins [alpha]v[beta]3 and [alpha]v[beta]5 promote adenovirus internalization but not virus attachment. *Cell* 73: 309-319.

16. Schiffelers, R. M., et al. (2003). Anti-tumor efficacy of tumor vasculature-targeted liposomal doxorubicin. *J. Controlled Release* 91: 115-122.

17. McCarthy, J. R., and Weissleder, R. (2008). Multifunctional magnetic nanoparticles for targeted imaging and therapy. *Adv Drug Delivery Rev* 60: 1241-1251.

18. Montet, X., Funovics, M., Montet-Abou, K., Weissleder, R., and Josephson, L. (2006). Multivalent effects of RGD peptides obtained by nanoparticle display. *J. Med. Chem.* 49: 6087-6093.

19. Dijkgraaf, I., et al. (2007). Improved targeting of the $\alpha_v\beta_3$ integrin by multimerisation of RGD peptides. *Eur. J. Nucl. Med. Mol. Imaging.* 34: 267-273.

20. Kiessling, L. L., Gestwicki, J. E., and Strong, L. E. (2006). Synthetic Multivalent Ligands as Probes of Signal Transduction. *Angew. Chem.* 45: 2348-2368.

21. Kok, R. J., et al. (2002). Preparation and Functional Evaluation of RGD-Modified Proteins as AVB3 Integrin Directed Therapeutics. *Bioconjug. Chem.* 13: 128-135.

22. Davis, M. E. (2002). Non-viral gene delivery systems. *Curr. Opin. Biotechnol.* 13: 128-131.

23. Erbacher, P., Remy, J. S., and Behr, J. P. (1999). Gene transfer with synthetic virus-like particles via the integrin-mediated endocytosis pathway. *Gene Ther* 6: 138-145.

24. Kunath, K., Merdan, T., Hegener, O., Haberlein, H., and Kissel, T. (2003). Integrin targeting using RGD-PEI conjugates for in vitro gene transfer. *J. Gene Med.* 5: 588-599.

25. Schiffelers, R. M., et al. (2004). Cancer siRNA therapy by tumor selective delivery with ligand-targeted sterically stabilized nanoparticle. *Nucleic Acids Res.* 32: e149.

26. Neu, M., Fischer, D., and Kissel, T. (2005). Recent advances in rational gene transfer vector design based on poly(ethylene imine) and its derivatives. *J Gene Med* 7: 992-1009.

27. Blessing, T., Kursa, M., Holzhauser, R., Kircheis, R., and Wagner, E. (2001). Different strategies for formation of pegylated EGF-conjugated PEI/DNA complexes for targeted gene delivery. *Bioconjug Chem* 12: 529-537.

28. Ogris, M., Brunner, S., Schuller, S., Kircheis, R., and Wagner, E. (1999). PEGylated DNA/transferrin-PEI complexes: reduced interaction with blood components, extended circulation in blood and potential for systemic gene delivery. *Gene Ther* 6: 595-605.

29. Kichler, A. (2004). Gene transfer with modified polyethylenimines. *J. Gene Med.* 6: S3-S10.

30. Levy, R., et al. (2004). Rational and Combinatorial Design of Peptide Capping Ligands for Gold Nanoparticles. *J. Am. Chem. Soc.* 126: 10076-10084.

31. Zanta, M. A., Boussif, O., Adib, A., and Behr, J. P. (1997). In Vitro Gene Delivery to Hepatocytes with Galactosylated Polyethylenimine. *Bioconjug. Chem.* 8: 839-844.

32. Ogris, M., Steinlein, P., Kursa, M., Mechtler, K., Kircheis, R., and Wagner, E. (1998). The size of DNA/transferrin-PEI complexes is an important factor for gene expression in cultured cells. *Gene Ther.* 5: 1425-1433.

33. Guo, W., and Lee, R. J. (1999). Receptor-Targeted Gene Delivery ViaFolate-Conjugated Polyethylenimine. *AAPS PharmSci.* 11: 19.

34. Diebold, S. S., Kursa, M., Wagner, E., Cotten, M., and Zenke, M. (1999). Mannose Polyethylenimine Conjugates for Targeted DNA Delivery into Dendritic Cells. *J. Biol. Chem.* 274: 19087-19094.

35. Bettinger, T., Remy, J. S., and Erbacher, P. (1999). Size Reduction of Galactosylated PEI/DNA Complexes Improves Lectin-Mediated Gene Transfer into Hepatocytes. *Bioconjug. Chem.* 10: 558-561.

36. Chiu, S.-J., Ueno, N. T., and Lee, R. J. (2004). Tumor-targeted gene delivery via anti-HER2 antibody (trastuzumab, Herceptin®) conjugated polyethylenimine. *J. Controlled Release* 97: 357-369.

37. Blessing, T., Kursa, M., Holzhauser, R., Kircheis, R., and Wagner, E. (2001). Different Strategies for Formation of PEGylated EGF-Conjugated PEI/DNA Complexes for Targeted Gene Delivery. *Bioconjug. Chem.* 12: 529-537.

38. Daniel, M. C., and Astruc, D. (2004). Gold nanoparticles: assembly, supramolecular chemistry, quantum-size-related properties, and applications toward biology, catalysis, and nanotechnology. *Chem. Rev.* 104: 293-346.

39. Ingram, R. S., Hostetler, M. J., and Murray, R. W. (1997). Poly-hetero-w;-functionalized Alkanethiolate-Stabilized Gold Cluster Compounds. *J. Am. Chem. Soc.* 119: 9175-9178.

40. Wang, Z., Levy, R., Fernig, D. G., and Brust, M. (2005). The Peptide Route to Multifunctional Gold Nanoparticles. *Bioconjug Chem* 16: 497-500.

41. Garanger, E., Boturyn, D., Jin, Z., Dumy, P., Favrot, M.-C., and Coll, J.-L. (2005). New Multifunctional Molecular Conjugate Vector for Targeting, Imaging, and Therapy of Tumors. *Mol. Ther.* 12: 1168-1175.

42. Carlson, C. B., Mowery, P., Owen, R. M., Dykhuizen, E. C., and Kiessling, L. L. (2007). Selective tumor cell targeting using low-affinity, multivalent interactions. *ACS Chem. Biol.* 2: 119-127.

43. Rejman, J., Conese, M., and Hoekstra, D. (2006). Gene Transfer by Means of Lipo- and Polyplexes: Role of Clathrin and Caveolae-Mediated Endocytosis. *J Liposome Res* 16: 237-247.

44. Ogris, M., Steinlein, P., Carotta, S., Brunner, S., and Wagner, E. (2001). DNA/polyethylenimine transfection particles: influence of ligands, polymer size, and PEGylation on internalization and gene expression. *AAPS PharmSci* 3: E21.

45. Luo, D., and Saltzman, W. M. (2000). Enhancement of transfection by physical concentration of DNA at the cell surface. *Nat Biotech* 18: 893-895.

46. Kopatz, I., Remy, J.-S., and Behr, J.-P. (2004). A model for non-viral gene delivery: through syndecan adhesion molecules and powered by actin. *J. Gene Med.* 6: 769-776.

47. French, A. J., Adams, C. A., Anderson, L. S., Kitchen, J. R., Hughes, M. R., and Wood, S. H. (2008). Development of Human cloned Blastocysts Following Somatic Cell Nuclear Transfer (SCNT) with Adult Fibroblasts. *Stem Cells.*

48. Mislick, K. A., and Baldeschwieler, J. D. (1996). Evidence for the role of proteoglycans in cation-mediated gene transfer. *Proc. Natl. Acad. Sci. U.S.A.* 93: 12349-12354.

49. Goodman, C. M., McCusker, C. D., Yilmaz, T., and Rotello, V. M. (2004). Toxicity of Gold Nanoparticles Functionalized with Cationic and Anionic Side Chains. *Bioconjug. Chem.* 15: 897-900.

50. Srivastava, I. K., et al. (2008). Comparative evaluation of trimeric envelope glycoproteins derived from subtype C and B HIV-1 R5 isolates. *Virology* 372: 273-290.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

---

What is claimed is:

1. A clustered ligand vehicle for delivery of a therapeutic agent to a target expressing a receptor, said vehicle comprising:

one or more nanoparticles, each nanoparticle bearing a plurality of ligands, wherein said plurality of ligands comprises a combination of CAP peptides, wherein said CAP peptide are peptides that comprise the amino acid sequence Cys-Cys-Val-Val-Val-Thr (Seq ID NO:1): and CAP-RGD peptides, wherein said CAP-RGD peptides are peptides that comprise the amino acid sequence Cys-Cys-Val-Val-Val-Thr-Arg-Gly-Asp (SEQ ID NO:2); and a carrier comprising said therapeutic agent, wherein each of the one or more nanoparticles is conjugated to the surface of the carrier.

2. The clustered ligand vehicle of claim 1, wherein said CAP peptide and CAP-RGD peptides comprise a peptide selected from the group consisting of Cys-Cys-Val-Val-Val-Thr (Cap) (SEQ ID NO:1), Cys-Cys-Val-Val-Val-Thr-Arg-Gly-Asp (Cap-RGD) (SEQ ID NO:2), Cys-Cys-Val-Val-Val-Thr-Arg-Gly-Asp-Azidosalicylic Acid (Cap-RGD-ASA) (SEQ ID NO:3), and Cys-Cys-Val-Val-Val-Thr-Azidosalicylic Acid (Cap-ASA) (SEQ ID NO:4) peptides.

3. The clustered ligand vehicle according to any one of claims 1 and 2, wherein the Cap peptides and Cap-RGD peptides are present in a ratio of from about 99:1 to about 85:15.

4. The clustered ligand of claim 3, wherein the ratio of Cap peptides to Cap-RGD peptides is selected to promote clustering.

5. The clustered ligand vehicle of claim 1, wherein said one or more nanoparticles are conjugated to the carrier by covalent bonding.

6. The clustered ligand vehicle of claim 1, wherein the carrier comprises a cationic polymer.

7. The clustered ligand vehicle of claim 1, wherein the carrier comprises poly(ethylene imine).

8. The clustered ligand vehicle of claim 1, wherein the therapeutic agent comprises an agent selected from the group consisting of DNA, interfering RNA, small inhibitory RNA, and a ribozyme.

9. The clustered ligand vehicle of claim 8, wherein the therapeutic agent comprises DNA.

10. The clustered ligand vehicle of claim 1, wherein the therapeutic agent comprises DNA and the carrier comprises poly(ethylene imine).

11. The clustered ligand vehicle of claim 1, wherein the clustered ligand vehicle is not larger than 200 nm in diameter.

12. The clustered ligand vehicle of claim 1, wherein said one or more nanoparticles comprise a material selected from the group consisting of a metal, a semiconductor, and carbon.

13. The clustered ligand vehicle of claim 1, wherein said one or more nanoparticles comprise gold.

14. The clustered ligand vehicle of claim 1, wherein said one or more nanoparticles are conjugated to the carrier by a cross-linker.

* * * * *